United States Patent [19]

Kay et al.

[11] Patent Number: 4,579,581
[45] Date of Patent: Apr. 1, 1986

[54] BIOLOGICALLY ACTIVE AMIDE DERIVATIVES

[75] Inventors: Ian T. Kay; David Bartholomew, both of Wokingham; Emyr G. Williams, Reading; Robert A. Noon, Cricklewood, all of England

[73] Assignee: Imperial Chemical Industries PLC, London, England

[21] Appl. No.: 582,640

[22] Filed: Feb. 22, 1984

Related U.S. Application Data

[62] Division of Ser. No. 353,006, Feb. 26, 1982, Pat. No. 4,447,446.

[30] Foreign Application Priority Data

Mar. 4, 1981 [GB] United Kingdom ............... 8106817
May 12, 1981 [GB] United Kingdom ............... 8114393

[51] Int. Cl.$^4$ .......................................... C07D 121/52
[52] U.S. Cl. ........................... 71/88; 564/74; 564/78; 564/154; 564/159; 564/158; 514/521; 514/522; 514/599; 514/616; 514/469; 514/471; 514/448; 514/365; 514/367; 514/354; 514/355; 71/90; 71/94; 71/98; 71/105; 71/118; 558/392; 558/313 CM
[58] Field of Search ............ 260/465 D, 465.4; 564/74, 78, 154, 159, 158; 514/521, 522, 599, 616, 469, 471, 448, 365, 367, 354, 355; 71/90, 94, 98, 105, 118

[56] References Cited

FOREIGN PATENT DOCUMENTS 0005591 11/1979 European Pat. Off. .
2139641 8/1971 Fed. Rep. of Germany .
1201358 8/1970 United Kingdom .
2037754 7/1980 United Kingdom .

OTHER PUBLICATIONS

CA, 66, 2503.t.
CA, 75, 35853.f.
Martin et al, *J. Org. Chem.*, 31 (11), 3612-15 (1966).
Ketcham et al, *J. Med. Chem.*, 1971, 14(5), 456-8.

Primary Examiner—Paul R. Michl
Assistant Examiner—Alex H. Walker
Attorney, Agent, or Firm—Cushman, Darby & Cushman

[57] ABSTRACT

Herbicidal and fungicidal benzamide derivatives of the formula (I)

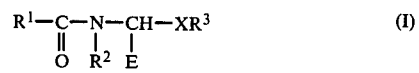

wherein $R^1$ is an optionally substituted alkyl, alkenyl, aryl, heterocyclyl, benzyl, or heterocyclylmethyl radical;
$R^2$ is hydrogen, or an optionally substituted alkyl, alkenyl, benzyl, or heterocyclylmethyl, radical;
X is oxygen, sulphur, or an —NH— group;
$R^3$ is an optionally substituted alkyl or alkenyl radical when X is oxygen or sulphur, or is an optionally substituted alkanoyl radical when X is —NH—;
and E is a —CN, —CONH$_2$, —CSNH$_2$, or —CONR$^4$R$^5$ group wherein each $R^4$ and $R^5$ is an optionally substituted alkyl or alkenyl group.

15 Claims, No Drawings

BIOLOGICALLY ACTIVE AMIDE DERIVATIVES

This is a division of U.S. application Ser. No. 353,006, filed Feb. 26, 1982, now U.S. Pat. No. 4,447,446.

This invention relates to substituted benzamide derivatives useful as herbicides and fungicides, to processes of combatting weeds and fungal infestations and to herbicidal and fungicidal compositions.

Substituted benzamide derivatives have previously been proposed for use as herbicides; by way of example, the compounds disclosed in U.K. Patent Specifications Nos. 1209608 and 1395802 may be mentioned.

According to the present invention, there are provided amide derivatives of the formula (I)

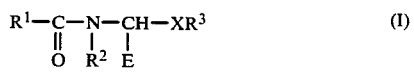

wherein $R^1$ is an optionally substituted alkyl, alkenyl, aryl, heterocyclyl, benzyl, or heterocyclylmethyl radical;

$R^2$ is hydrogen, or an optionally substituted alkyl, alkenyl, benzyl, or heterocyclylmethyl, radical;

X is oxygen, sulphur, or an —NH— group;

$R^3$ is an optionally substituted alkyl or alkenyl radical when X is oxygen or sulphur, or is an optionally substituted alkanoyl radical when X is —NH—;

and E is a —CN, —CONH$_2$, —CSNH$_2$, or —CONR$^4$R$^5$ group wherein each $R^4$ and $R^5$ is hydrogen or an optionally substituted alkyl or alkenyl group.

When the group $R^1$ is an optionally substituted alkyl or alkenyl radical, it may be for example $C_{1-5}$ alkyl or $C_{3-5}$ alkenyl radical. Examples of substituents include $C_1$-$C_4$ alkoxy, $C_1$-$C_4$ alkylthio and halogen (i.e. fluorine, chlorine, bromine or iodine).

When $R^1$ is a benzyl radical optionally substituted in the phenyl ring, examples of substituents include halogen (fluorine, chlorine, bromine or iodine), $C_1$-$C_4$ alkoxy, $C_1$-$C_4$ alkylthio, nitro, cyano, $C_1$-$C_4$ haloalkyl (e.g. CF$_3$), and $C_1$-$C_4$ alkyl (e.g. CH$_3$). There may be from one to five substituents, which may be the same or different.

When $R^1$ is an optionally substituted aryl group it may be a phenyl or naphthyl radical. Examples of substituents which may be present include fluorine, chlorine, bromine, iodine, $C_1$-$C_4$ alkoxy, methylenedioxy and ethylenedioxy, $C_1$-$C_4$ alkyl, $C_1$-$C_4$ alkylthio, $C_1$-$C_4$ haloalkyl (e.g. CF$_3$) nitro and cyano. There may be from one to three or more substituents which may be the same or different. When $R^1$ is a substituted phenyl radical the substituents are preferably in the 3, 4, or 5 positions. When a methylenedioxy or ethylenedioxy substituent is present, it preferably is attached to the 3 and 4 positions of the phenyl ring. A halogen substituent (e.g. Cl or Br) may also be present in the 4- or 5-position, or both, in such compounds.

When $R^1$ is an optionally substituted heterocyclyl radical, it may for example be a furyl, benzfuryl, thienyl, pyridyl, thiazolyl, or benzthiazolyl radical. Examples of substituents which may be present include those listed above for the case when $R^1$ is a substituted phenyl radical. There may be from one to three or more substituents which may be the same or different.

When $R^1$ is an optionally substituted heterocyclylmethyl radical, the heterocyclyl group may be for example a furyl, thienyl, pyridyl, thiazolyl or benzothiazolyl group. Examples of substituents which may be present in the heterocyclyl group include those described above for the case when $R^1$ is a substituted phenyl radical.

$R^2$ is preferably hydrogen but when it is not, then it may be an optionally substituted alkyl group, for example an $C_1$-$C_4$ alkyl group. Examples of substituents which may be present include fluorine, chlorine, bromine, iodine, and $C_1$-$C_4$ alkoxy. When $R^2$ is an optionally substituted alkenyl group it may be for example an alkenyl group of from 3–5 carbon atoms. Examples of substituents which may be present include those listed above for the case when $R^2$ is an alkyl group.

When $R^2$ is an optionally substituted benzyl group, the substituents may include those described above for the case when $R^1$ is substituted benzyl.

When $R^2$ is an optionally substituted heterocyclylmethyl group, the heterocyclyl ring may be for example a furyl, thienyl, pyridyl, thiazolyl, or benzothiazolyl ring. Substituents which may be present include those described above for the case where $R^1$ is a substituted phenyl radical.

When $R^3$ is an optionally substituted alkyl or alkenyl radical it may have any of the values described above for the group $R^2$.

When $R^3$ is an alkanoyl group (i.e. when X is NH) it may for example have from 1 to 4 carbon atoms (e.g. it may be a formyl, acetyl, or propionyl group).

$R^4$ and $R^5$ are preferably hydrogen, but when they are not, they may be optionally substituted alkyl or alkenyl group it may have any of the values defined above for the group $R^2$ when it is an optionally substituted alkyl or alkenyl radical.

Within the above definition, one sub-class of compounds according to the invention comprises those compounds wherein $R^2$ is hydrogen. Within this sub-class, a further sub-class comprises those compounds in which E is a cyano group, X is O or S, and $R^3$ is $C_1$-$C_4$ alkyl A group within the latter sub-class includes those compounds in which $R^1$ is phenyl or heterocyclyl. Within the latter group, a sub-group includes compounds in which the heterocyclyl or phenyl group is substituted, for example by alkyl, alkoxy, methylenedioxy, or halogen, for example fluorine or chlorine. In such compounds the groups or atoms are preferably located in the 3, 4 or 5 positions of the phenyl ring.

The structural formula (I) given above is believed to be the one which best represents the structure of the compounds. For some compounds within the scope of the formula (I) it may be possible in principle for tautomeric forms of the compound to exist, in which a hydrogen atom is transposed to another part of the molecule and the chemical bonds between the atoms of the molecule are consequently rearranged; thus, where $R^1$ is hydrogen, it is possible in principle for the molecule to exist in the alternative form (II)

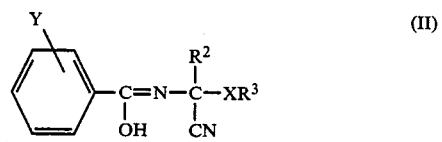

The structural formula (I) is intended to represent and include such tautomeric forms, insofar as they may exist. The structural formula (I) is also intended to include any physically distinguishable modifications of the compounds which may arise, for example, from different ways in which the molecules are arranged in a crystal lattice, or from the inability of parts of the molecules to rotate freely in relation to other parts, or from geometrical and or optical isomerism, or from intramolecular or inter-molecular bonding, or otherwise.

Particular examples of compounds according to the invention are listed in Table I below:

TABLE 1

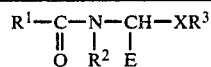

| COMPOUND NO | $R^1$ | $R^2$ | $XR^3$ | E | Route | Melting Point °C. | Notes (see end of Table) |
|---|---|---|---|---|---|---|---|
| 1 | $C_6H_5$ | H | OMe | CONHMe | A | 155 | |
| 2 | $C_6H_5$ | H | OMe | CN | A | 83 | |
| 3 | $C_6H_5$ | H | OEt | $CONH_2$ | A | 148–150 | |
| 4 | $C_6H_5$ | H | OEt | CN | A | 107–110 | |
| 5 | $C_6H_5$ | H | $OPr^n$ | $CONH_2$ | A | 105–108 | |
| 6 | $C_6H_5$ | H | $OPr^i$ | $CONH_2$ | A | 119–121 | |
| 7 | $C_6H_5$ | H | $OBu^n$ | $CONH_2$ | A | 85–88 | |
| 8 | $C_6H_5$ | H | $OPr^i$ | CN | A | 118–119 | |
| 9 | $C_6H_5$ | H | $OBu^n$ | CN | A | 74–77 | |
| 10 | $C_6H_5$ | H | $OBu^t$ | $CONH_2$ | A | 150–154 | |
| 11 | $C_6H_5$ | H | $OBu^s$ | $CONH_2$ | A | 94–95 | |
| 12 | $C_6H_5$ | H | $OBu^t$ | CN | A | 117–120 | |
| 13 | $C_6H_5$ | H | $OBu^s$ | CN | A | 77–79 | |
| 14 | $4\text{-Cl.}C_6H_4.$ | H | OMe | $CONH_2$ | A | 164–166 | |
| 15 | $4\text{-Cl.}C_6H_4.$ | H | OMe | CN | A | 123–125 | |
| 16 | $2\text{-Cl.}C_6H_4.$ | H | OMe | $CONH_2$ | A | 110–112 | |
| 17 | $2\text{-Cl.}C_6H_4.$ | H | OMe | CN | A | 86–89 | |
| 18 | $3,5\text{-Cl}_2.C_6H_3.$ | H | OMe | CN | A | 155–158 | |
| 19 | $3\text{-Cl.}C_6H_4.$ | H | OMe | $CONH_2$ | A | 135–137 | |
| 20 | $3\text{-Cl.}C_6H_4.$ | H | OMe | CN | A | 90–92 | |
| 21 | $3,5(Me)_2.C_6H_3.$ | H | OMe | $CONH_2$ | A | 171–173 | |
| 22 | $3,5(Me)_2.C_6H_3.$ | H | OMe | CN | A | 107–108 | |
| 23 | $3,5\text{-Cl}_2.C_6H_3.$ | H | OMe | $CONH_2$ | A | 190–192 | |
| 24 | $C_6H_5$ | H | $OPr^n$ | CN | A | 91–93 | |
| 25 | $3\text{-CF}_3.C_6H_4.$ | H | OEt | $CONH_2$ | A | 151–153 | |
| 26 | $3\text{-CF}_3.C_6H_4.$ | H | OEt | CN | A | 54–56 | |
| 27 | $3\text{-NO}_2.C_6H_4.$ | H | OEt | $CONH_2$ | A | 150–152 | |
| 28 | $3\text{-NO}_2.C_6H_4.$ | H | OEt | CN | A | 99–100 | |
| 29 | $3\text{-Me.}C_6H_4.$ | H | OEt | $CONH_2$ | A | 123–125 | |
| 30 | $3\text{-Me.}C_6H_4.$ | H | OEt | CN | A | 76–77 | |
| 31 | $3,5\text{-Cl}_2.C_6H_3.$ | H | OEt | $CONH_2$ | A | 188–189 | |
| 32 | $3,5\text{-Cl}_2.C_6H_3.$ | H | $OPr^i$ | $CONH_2$ | A | 178–180 | |
| 33 | $3,4\text{-Cl}_2.C_6H_3.$ | H | OEt | CN | A | 96–97 | |
| 34 | $3,5\text{-Cl}_2.C_6H_3.$ | H | OEt | CN | A | 156 | |
| 35 | $3\text{-Br.}C_6H_4.$ | H | OEt | $CONH_2$ | A | 152–153 | |
| 36 | $3\text{-Br.}C_6H_4.$ | H | OEt | CN | A | 93–95 | |
| 37 | $3\text{-MeO.}C_6H_4.$ | H | OEt | $CONH_2$ | B | 143–144 | |
| 38 | $3\text{-MeO.}C_6H_4.$ | H | OEt | CN | B | 72 | |
| 39 | $3,5\text{-Cl}_2.C_6H_3.$ | H | $OPr^i$ | CN | A | 128–130 | |
| 40 | $3\text{-Cl.}C_6H_4.$ | H | SMe | CN | A | 115–117 | |
| 41 | $3\text{-Cl.}C_6H_4.$ | H | OEt | CN | A | 90–91 | |
| 42 | $3,5\text{-(CF}_3)_2.C_6H_3.$ | H | OEt | CN | A | 114–116 | |
| 43 | $3\text{-Cl.}C_6H_4.$ | H | $OPr^i$ | CN | A | 82–84 | |
| 44 | $3\text{-Cl.}C_6H_4.$ | H | OEt | $CSNH_2$ | G | 136–137 | |
| 45 | $2,5\text{-Cl}_2.C_6H_4.$ | H | OEt | CN | A | 123–124 | |
| 46 | $3,5\text{-Cl}_2.C_6H_3.$ | H | $OCH_2CF_3$ | $CONH_2$ | A | 204–205 | |
| 47 | $3,4\text{-Cl}_2.C_6H_3.$ | H | OEt | $CSNH_2$ | G | 140 | |
| 48 | $3\text{-F.}C_6H_4.$ | H | OEt | $CONH_2$ | A | 112–113 | |
| 49 | $3\text{-F.}C_6H_4.$ | H | OMe | $CONH_2$ | A | 137–139 | |
| 50 | $2,6\text{-(Me)}_2.C_6H_3.$ | H | OMe | CN | B | 65–67 | |
| 51 | $3\text{-F.}C_6H_4.$ | H | OEt | CN | A | 68–69 | |
| 52 | $3\text{-F.}C_6H_4.$ | H | OMe | CN | A | 86–88 | |
| 53 | $C_6H_5$ | Me | OMe | CN | F | Oil | a |
| 54 | $3\text{-Cl.}C_6H_4.$ | Me | OEt | CN | F | Oil | b |
| 55 | $3\text{-Cl.}C_6H_4.$ | Me | OMe | CN | F | 55–56 | |
| 56 | $3\text{-Cl.}C_6H_4.$ | H | OEt | $CONH_2$ | A | 134–136 | |
| 57 | $3,5(CF_3)_2.C_6H_3.$ | H | OEt | $CONH_2$ | A | 204–206 | |
| 58 | $3\text{-Cl.}C_6H_4.$ | H | $OPr^i$ | $CONH_2$ | A | 140–143 | |
| 59 | $2,5\text{-Cl}_2.C_6H_3.$ | H | OEt | $CONH_2$ | A | 163–165 | |
| 60 | $3\text{-F.}C_6H_4.$ | H | $OPr^i$ | $CONH_2$ | A | 140 | |
| 61 | $3\text{-F.}C_6H_4.$ | H | $OPr^i$ | CN | A | 82–83 | |
| 62 | $3\text{-Me.}C_6H_4.$ | H | OMe | CN | B | 68–71 | |
| 63 | $3\text{-Me.}C_6H_4.$ | H | $OPr^i$ | CN | B | 86–87 | |
| 64 | $3,5\text{-Cl}_2.C_6H_3.$ | Me | OMe | CN | F | 88–90 | |
| 65 | $3,5\text{-Cl}_2.C_6H_3.$ | Me | OEt | CN | F | 46–48 | |
| 66 | $3,5(Me)_2.C_6H_3.$ | H | OEt | CN | B | 85–87 | |
| 67 | $F_5.C_6.$ | H | OEt | CN | A | 85–86 | |
| 68 | $3\text{-Me}-4\text{-NO}_2.C_6H_3.$ | H | OEt | $CONH_2$ | A | 116–118 | |
| 69 | $4\text{-MeO}-3,5\text{-Cl}_2.C_6H_2.$ | H | OEt | CN | B | 119–122 | |

TABLE 1-continued $$R^1-\underset{\underset{O}{\|}}{C}-\underset{\underset{R^2}{|}}{N}-\underset{\underset{E}{|}}{CH}-XR^3$$

| COMPOUND NO | $R^1$ | $R^2$ | $XR^3$ | E | Route | Melting Point °C. | Notes (see end of Table) |
|---|---|---|---|---|---|---|---|
| 70 | 3-Me.C$_6$H$_4$. | H | OMe | CSNH$_2$ | G | 130–131 | |
| 71 | 3,5-(Me)$_2$.C$_6$H$_3$. | H | OEt | CSNH$_2$ | G | 170–171 | |
| 72 | 3,5-Cl$_2$.C$_6$H$_3$. | Pr$^i$ | OMe | CN | F | 79–81 | |
| 73 | 3,5-Cl$_2$.C$_6$H$_3$. | Et | OMe | CN | F | 97–98 | |
| 74 | 3-Cl.C$_6$H$_4$. | Et | OMe | CN | F | Oil | c |
| 75 | 3-Cl.C$_6$H$_4$. | Pr$^i$ | OMe | CN | F | Oil | d |
| 76 | 3-Me.C$_6$H$_4$. | Pr$^i$ | OMe | CN | F | Oil | e |
| 77 | 3-Me.C$_6$H$_4$. | Et | OMe | CN | F | Oil | f |
| 78 | 3-Me.C$_6$H$_4$. | Me | OMe | CN | F | Oil | g |
| 79 | 3,5(Me)$_2$.C$_6$H$_3$. | H | OEt | CONH$_2$ | B | 180–183 | |
| 80 | 3-CN.C$_6$H$_4$. | H | OEt | CONH$_2$ | A | 157–158 | |
| 81 | 3-CN.C$_6$H$_4$. | H | OEt | CN | A | 112–115 | |
| 82 | 3,5-Cl$_2$.C$_6$H$_3$. | H | OPr$^n$ | CONH$_2$ | A | 178–180 | |
| 83 | 3,5-Cl$_2$.C$_6$H$_3$. | H | OPr$^n$ | CN | A | 137–138 | |
| 84 | 3,5-Cl$_2$.C$_6$H$_3$. | H | OPr$^n$ | CSNH$_2$ | G | 137–138 | |
| 85 | 2-naphthyl | H | OEt | CN | A | 117–118 | |
| 86 | 3-Cl—5-NO$_2$.C$_6$H$_3$. | H | OEt | CN | A | 133–136 | |
| 87 | 3-chlorobenzyl | H | OEt | CN | B | 87–89 | |
| 88 | 2,6-dichloro-4-pyridyl- | H | OMe | CONH$_2$ | B | 190–192 | |
| 89 | 3-Cl.C$_6$H$_4$. | H | OCH$_2$CH=CH$_2$ | CONH$_2$ | A | 91–92 | |
| 90 | 3,5-Cl$_2$.C$_6$H$_3$. | H | OCH$_2$CH=CH$_2$ | CONH$_2$ | A | 164–165 | |
| 91 | 3,5-Cl$_2$.C$_6$H$_3$. | H | OCH$_2$CH=CH$_2$ | CN | A | 134–135 | |
| 92 | 3-Cl.C$_6$H$_4$. | H | OCH$_2$CH=CH$_2$ | CN | A | 64–66 | |
| 93 | 3-Cl.C$_6$H$_4$. | H | SMe | CONH$_2$ | A | 154–156 | |
| 94 | 3-Br.C$_6$H$_4$. | H | OMe | CONH$_2$ | A | 141–143 | |
| 95 | 3-Br.C$_6$H$_4$. | H | OMe | CN | A | 88–90 | |
| 96 | 3-Et.C$_6$H$_4$. | H | OEt | CN | B | 55–56 | |
| 97 | 3-Cl—5-Me.C$_6$H$_3$. | H | OEt | CN | B | 114–116 | |
| 98 | 3-Cl—5-Me.C$_6$H$_3$. | H | OMe | CN | B | 99–102 | |
| 99 | 2-furyl | H | OMe | CONH$_2$ | B | 113–114 | |
| 100 | 2-furyl | H | OEt | CONH$_2$ | B | 113–114 | |
| 101 | 2-furyl | H | OMe | CN | B | 75–77 | |
| 102 | 2-furyl | H | OEt | CN | B | 73–74 | |
| 103 | 2,6-dichloro-4-pyridyl- | H | OMe | CN | B | 134–136 | |
| 104 | 2-benzthiazolyl | H | OMe | CN | B | 116–118 | |
| 105 | iso-pentyl | H | OMe | CONH$_2$ | B | 98–101 | |
| 106 | iso-pentyl | H | OMe | CN | B | Oil | |
| 107 | tert-C$_4$H$_9$ | H | OMe | CONH$_2$ | B | 86–88 | |
| 108 | tert-C$_4$H$_9$ | H | OMe | CN | B | 59–60 | |
| 109 | 3,5-Cl$_2$.C$_6$H$_3$. | H | SMe | CN | A | 150–152 | |
| 110 | 3-Me.C$_6$H$_4$. | H | SMe | CN | B | 119–120 | |
| 111 | 3-Br.C$_6$H$_4$. | H | OEt | CSNH$_2$ | G | 145–146 | |
| 112 | 2-naphthyl | H | OMe | CN | A | 117–118 | |
| 113 | 3-MeO.C$_6$H$_4$. | H | OMe | CONH$_2$ | B | 106–108 | |
| 114 | 3-Cl—5-NO$_2$.C$_6$H$_3$. | H | OEt | CONH$_2$ | A | 190–192 | |
| 115 | 5-Cl—2-MeO.C$_6$H$_3$. | H | OEt | CONH$_2$ | B | 177–180 | |
| 116 | 5-Cl—2-MeO.C$_6$H$_3$. | H | OEt | CN | B | 109–112 | |
| 117 | 3,5-Cl$_2$.C$_6$H$_3$. | H | OCH$_2$CF$_3$ | CN | A | 148–149 | |
| 118 | 3-MeO.C$_6$H$_4$. | H | OMe | CN | B | 80–81 | |
| 119 | 3,5(MeO)$_2$.C$_6$H$_3$. | H | OMe | CN | B | 98–100 | |
| 120 | 3,5(MeO)$_2$.C$_6$H$_3$. | H | OEt | CN | B | 86–88 | |
| 121 | C$_6$H$_5$CH$_2$. | H | OMe | CN | B | 67–68 | |
| 122 | 3-F.C$_6$H$_4$. | Me | OMe | CN | F | Oil | h |
| 123 | 3-I.C$_6$H$_4$. | H | OEt | CONH$_2$ | A | 174–176 | |
| 124 | 3-I.C$_6$H$_4$. | H | OMe | CONH$_2$ | A | 147–148 | |
| 125 | 3-I.C$_6$H$_4$. | H | OEt | CN | A | 123–125 | |
| 126 | 3-I.C$_6$H$_4$. | H | OMe | CN | A | 98–101 | |
| 127 | 3,5-Cl$_2$.C$_6$H$_3$. | CH$_2$Ph | OMe | CN | F | 59–61 | |
| 128 | 3-Cl.C$_6$H$_4$. | CH$_2$Ph | OMe | CN | F | Oil | i |
| 129 | 3,5-Cl$_2$.C$_6$H$_3$. | H | OEt | CONHMe | B | 184–185 | |
| 130 | 3,5-Cl$_2$.C$_6$H$_3$. | H | OEt | CONMe$_2$ | B | 90–92 | |
| 131 | 3,5-Cl$_2$.C$_6$H$_3$. | H | OEt | CO—N(piperidyl) | B | 112–113 | |
| 132 | 3-Cl—5-Me.C$_6$H$_3$. | H | OEt | CONH$_2$ | B | 169–171 | |
| 133 | 3,5-F$_2$.C$_6$H$_3$. | H | OEt | CONH$_2$ | A | 173–175 | |
| 134 | 3,5-F$_2$.C$_6$H$_3$. | H | OEt | CN | A | 111–112 | |
| 135 | 3-Cl—4,5-F$_2$.C$_6$H$_2$. | H | OEt | CONH$_2$ | A | 167–168 | |
| 136 | 3-Cl—4,5-F$_2$.C$_6$H$_2$. | H | OEt | CN | A | 146–149 | |

TABLE 1-continued $$R^1-\underset{\underset{O}{\|}}{C}-\underset{\underset{R^2}{|}}{N}-\underset{\underset{E}{|}}{CH}-XR^3$$

| COMPOUND NO | R¹ | R² | XR³ | E | Route | Melting Point °C. | Notes (see end of Table) |
|---|---|---|---|---|---|---|---|
| 137 | $C_6H_5$. | H | NHAc | $CONH_2$ | D | 243–245 | |
| 138 | $C_6H_5$. | H | NHAc | CN | D | 193–194 | |
| 139 | $C_6H_5$. | H | NHAc | CONHMe | D | 207–209 | |
| 140 | $3,5\text{-}Br_2.C_6H_3$. | H | OEt | $CONH_2$ | A | 203–205 | |
| 141 | $3,5\text{-}Br_2.C_6H_3$. | H | OEt | CN | A | 165–167 | |
| 142 | $3,5\text{-}Cl_2.C_6H_3$. | $CH_2Ph$ | OEt | CN | F | Oil | j |
| 143 | $3\text{-}Eto.C_6H_4$. | H | OEt | $CONH_2$ | B | | |
| 144 | $3\text{-}Eto.C_6H_4$. | H | OEt | CN | B | 95–97 | |
| 145 | $3,4,5\text{-}Cl_3.C_6H_2$. | H | OEt | $CONH_2$ | A | 203–204 | |
| 146 | $3,4,5\text{-}Cl_3.C_6H_2$. | H | OEt | CN | A | 139–141 | |
| 147 | $3,5\text{-}Cl_2.C_6H_3$. | H | $OCH_2CH_2CH_2Cl$ | $CONH_2$ | A | 169–172 | |
| 148 | $3,5\text{-}Cl_2.C_6H_3$. | H | $OCH_2CH_2CH_2Cl$ | CN | A | 123–124 | |
| 149 | $3\text{-}F.C_6H_4$. | H | NHAc | $CONH_2$ | D | 238–240 | |
| 150 | $C_6H_5$. | $CH_2Ph$ | OMe | CN | F | Oil | |
| 151 | $3\text{-}F.C_6H_4$. | $CH_2Ph$ | OMe | CN | F | Oil | k |
| 152 | $3,5\text{-}Cl_2.C_6H_3$. | H | NHAc | $CONH_2$ | D | 267–268 | |
| 153 | $3,5\text{-}Cl_2.C_6H_3$. | H | NHAc | CN | D | 227–228 | |
| 154 | $3,5\text{-}Me_2.C_6H_3$. | H | NHAc | $CONH_2$ | C | 244–245 | |
| 155 | $3\text{-}F.C_6H_4$. | H | NHAc | CN | D | 175–176 | |
| 156 | $3,5\text{-}Me_2.C_6H_3$. | $CH_2Ph$ | OMe | CN | F | Oil | k |
| 157 | $3\text{-}Me.C_6H_4$. | $CH_2Ph$ | OMe | CN | F | Oil | l |
| 158 | $3,5\text{-}Me_2.C_6H_3$. | H | NHAc | CN | C | 195–197 | |
| 159 | $3,5\text{-}Cl_2.C_6H_3$. | 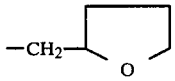 | OMe | CN | E | 89–90 | |
| 160 | $3,5\text{-}F_2.C_6H_3$. | $CH_2Ph$ | OMe | CN | F | Oil | m |
| 161 | $3\text{-}Cl.C_6H_4$. | 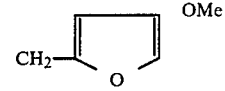 | OMe | CN | E | 48–49 | |
| 162 | $3,5\text{-}Me_2.C_6H_3$. | H | $NHCOCH=CH_2$ | $CONH_2$ | C | 201–203 | |
| 163 | $3,5\text{-}Me_2.C_6H_3$. | H | $NHCOCH=CH_2$ | CN | C | 191–193 | |
| 164 | $3,5\text{-}Cl_2C_6H_3$. | H | $NHCOCH=CH_2$ | $CONH_2$ | C | 223–225 | |
| 165 | $3,5\text{-}Cl_2C_6H_3$. | H | $NHCOCH=CH_2$ | CN | C | 220–222 | |
| 166 | $3,4,5\text{-}F_3C_6H_2$. | H | OEt | $CONH_2$ | A | 155–156 | |
| 167 | $3,4,5\text{-}F_3C_6H_2$. | H | OEt | CN | A | 129–131 | |
| 168 | $3,5\text{-}Cl_2.C_6H_3$. | Allyl | OMe | $CONH_2$ | E | 176–178 | |
| 169 | $3,5\text{-}Cl_2.C_6H_3$. | Allyl | OMe | CN | E | Oil | |
| 170 | $3,5\text{-}Cl_2.C_6H_3$. | $C_6H_5$ | OMe | CN | E | Oil | |
| 171 | $3,5\text{-}F_2C_6H_3$ | H | NHAC | $CONH_2$ | C | 197–200 | |
| 172 | $3,4\text{-}OCH_2O.C_6H_3$ | H | OEt | $CONH_2$ | B | 159–161 | |
| 173 | $3,4,5\text{-}F_3C_6H_2$ | H | $OCH_2CH=CH_2$ | $CONH_2$ | A | 104–106 | |
| 174 | $3,4,5\text{-}F_3C_6H_2$ | H | $OCH_2CH=CH_2$ | CN | A | 109–111 | |
| 175 | $3,4\text{-}OCH_2OC_6H_3$ | H | OEt | CN | B | 155–156 | |
| 176 | $3\text{-}ClC_6H_4$ | Allyl | OMe | $CONH_2$ | E | 115–116 | |
| 177 | $3\text{-}ClC_6H_4$ | $CH_2CH=CH_2$ | OMe | CN | E | Oil | |
| 178 | $2\text{-}HOC_6H_4$. | H | OEt | CN | B | Oil | |
| 179 | $2\text{-}ACOC_6H_4$ | H | OEt | CN | B | 83–87 | |
| 180 | $3\text{-}FC_6H_4$ | H | $OCH_2CF_3$ | $CONH_2$ | A | 104–106 | |
| 181 | $3\text{-}FC_6H_4$ | H | $OCH_2CF_3$ | CN | A | 106–107 | |
| 182 | $3,4,5\text{-}F_3C_6H_2$ | H | NHAC | $CONH_2$ | C | 241–242 | |
| 183 | $3,4,5\text{-}F_3C_6H_2$ | H | NHAC | CN | C | 210–211 | |
| 184 | $3,5\text{-}Cl_2C_6H_3$ | H | $OCH_2CH_2Br$ | $CONH_2$ | A | 165–166 | |
| 185 | $3,5\text{-}F_2C_6H_3$ | H | $OCH_2CH_2Br$ | $CONH_2$ | A | 160–162 | |
| 186 | $3,5\text{-}F_2C_6H_3$ | H | NHAC | CN | C | 204–206 | |
| 187 | $3\text{-}FC_6H_4$ | H | $\underset{\underset{CH_2}{\overset{\|}{CH}}}{NHCOCH_2}$ | CN | C | 185–187 | |
| 188 | $3,5\text{-}Cl_2C_6H_3$ | H | $OCH_2CH_2Cl$ | $CONH_2$ | A | 176–178 | |
| 189 | $4\text{-}MeOC_6H_4$ | H | OEt | $CONH_2$ | B | 169–170 | |
| 190 | $4\text{-}MeOC_6H_4$ | H | OEt | CN | B | 87–89 | |
| 191 | $3,4\text{-}OCH_2OC_6H_3$ | H | SMe | $CONH_2$ | B | 185–187 | |
| 192 | $3,4\text{-}OCH_2OC_6H_3$ | H | SMe | CN | B | 139–141 | |

TABLE 1-continued $$R^1-\underset{\underset{O}{\|}}{C}-\underset{R^2}{N}-\underset{E}{CH}-XR^3$$

| COMPOUND NO | R¹ | R² | XR³ | E | Route | Melting Point °C. | Notes (see end of Table) |
|---|---|---|---|---|---|---|---|
| 193 | 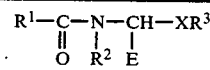 | H | OMe | CONH₂ | B | 214-215 | |
| 194 | 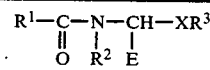 | H | OMe | CN | B | 110-111 | |
| 195 | 3-ClC₆H₄ | Me | SMe | CN | F | Oil | |
| 196 | 4-MeC₆H₄ | H | OEt | CN | B | 133-135 | |
| 197 | 4-ClC₆H₄ | H | OEt | CN | A | 102-103 | |
| 198 | 3,4-Me₂C₆H₃ | H | OEt | CN | A | 94-96 | |
| 199 | 4-BrC₆H₄ | H | OEt | CN | A | 113-114 | |
| 200 | 4-CNC₆H₄ | H | OEt | CN | A | 103-104 | |
| 201 | 3,4(MeO)₂C₆H₃ | H | OEt | CN | B | 121-123 | |
| 202 | 3-Cl—4-HOC₆H₃ | H | OEt | CN | B | 90-92 | |
| 203 | 3-Cl—4-ACOC₆H₃ | H | OEt | CN | B | 126-128 | |
| 204 | 3-Cl—4-Me—C₆H₃ | H | OEt | CN | A | 113-114 | |
| 205 | 3,5-Cl₂—4-Me C₆H₂ | H | OEt | CN | A | | |
| 206 | 4-CF₃C₆H₄ | H | OEt | CN | A | 114-115 | |
| 207 | 3-Cl—4-OMeC₆H₃ | H | OEt | CN | B | | |
| 208 | 3-Br—4-OMeC₆H₃ | H | OEt | CN | B | | |
| 209 | 3,4,5-Me₃C₆H₂ | H | OEt | CN | B | | |
| 210 | 4-EtC₆H₄ | H | OEt | CN | A | 115-116 | |

NOTES

The abbreviations used in Table I are standard chemical symbols. Thus the symbols Me, Et, Pr and Ph stand for methyl, ethyl, propyl, and phenyl groups respectively, and the symbols F₅.C₆. and 3-Cl-5-NO₂.C₆H₃., for example, stand for pentafluorophenyl and 3-chloro-5-nitrophenyl respectively.

Melting points are given for most compounds in the table. Where the compound is an oil, a refractive index measurement or nuclear magnetic resonance (NMR) data are given in the notes below. In the NMR information, the symbols have the following meanings:
s: singlet
t: triplet
q: quartet
multiplet
d: doublet Chemical shifts(δ) are quoted relative to tetramethylsilane. The solvent used was deuterochloroform.

Notes for individual compounds follow:
(a) Refractive index $n_D^{21}$=1.5233.
(b) Refractive index $n_D^{21}$=1.5197.
(c) NMR data: δ=1.3 (3H, t), 3.45 (3H, s), 3.7 (2H, q), 5.95 (H, S, broad), ca 7.5 (4H, m).
(d) NMR data: δ=1.5 (6H, d), 2.35 (3H, s), 3.3 (3H, s), 4.1 (1H, m), 5.5 (1H, s), ca. 7.2 (4H, m).
(e) NMR data: δ=1.5 (6H, d), 2.35 (3H, s), 3.3 (3H, s), 4.1 (1H, m), 5.5 (1H, s), ca. 7.2 (4H, m).
(f) NMR data: δ=1.3 (3H, t), 2.4 (3H, s), 3.7 (2H, q), 5.95 (1H, s, broad), ca. 7.3 (4H, m).
(g) NMR data: δ=2.4 (3H, s), 3.1 (3H, s), 3.4 (3H, s), ca. 6.1 (1H, s, very broad), ca. 7.3 (4H, m).
(h) NMR data: δ=3.1 (3H, s), 3.4 (3H, s), 6.1 (s, very broad), ca. 7.2 (4H, m).
(i) NMR data: δ=3.4 (3H, s), 4.75 (2H, s), 5.9 (1H, s), ca. 7.3 (9H, m).
(j) NMR data: δ=1.2 (3H, t), 3.55 (2H, q), 4.7 (2H, d), 5.95 (1H, broad), ca. 7.2 (8H, m).
(k) NMR data: 67 =3.35 (3H, s), 4.75 (2H, s), 5.9 (1H, s, broad), ca. 7.2 (9H, m).
(l) NMR data: δ=2.3 (6H, s), 3.3 (3H, s), 4.75 (2H, s) 5.9 (1H, s, broad), 7.0-7.4 (8H, m).
(m) NMR data: δ=3.4 (3H, s), 4.75 (2H, s), 5.9 (1H, s, broad), ca. 6.8-7.3 (8H, m).

In another aspect of the invention provides a process of inhibiting the growth of unwanted plants, which comprises applying to the plants, or to the locus thereof, a phytotoxic amount of a compound of the formula (I) as hereinbefore defined. The amount of the compound may vary, depending upon the identity of the particular compound chosen and the plant species whose growth is to be inhibited, but in general amounts of from 0.01 to 5.0 kilograms per hectare will be suitable; usually the amount will be from 0.2 to 1.0 kilograms per hectare. The skilled worker in the herbicide art will readily be able to establish appropriate application rates by standard procedures without undue experimentation.

The compounds of the invention are relatively less toxic towards certain crop plants than they are towards other plant species; accordingly, there is the possibility of using the compounds for selective weed control in these crops. Examples of such crops include cotton, sugar beet, rape, lettuce, peas; the compounds may be useful in a number of crops of families Compositae and Leguminosae.

The compounds used in the process of the invention are preferably applied in the form of a composition, in which the active ingredient is mixed with a carrier comprising a solid or liquid diluent. In another aspect, therefore, the invention provides a herbicidal composition, comprising as an active ingredient a compound of the formula (I) as hereinbefore defined, in admixture with a solid or liquid diluent. Preferably the composition also comprises a surface-active agent.

The solid compositions of the invention may be for example, in the form of dusting powders, or may take the form of granules. Suitable solid diluents include, for example, kaolin, bentonite, kieselguhr, dolomite, calcium carbonate, talc, powdered magnesia, and Fuller's Earth.

Solid compositions may also be in the form of dispersible powders or grains comprising in addition to the active ingredient, a wetting agent to facilitate the dispersion of the powder or grains in liquids. Such powders or grains may include fillers, suspending agents and the like.

Liquid compositions include aqueous solutions, dispersions and emulsions containing the active ingredient preferably in the presence of one or more surface active agents. Water or organic liquids may be used to prepare solutions, dispersions, or emulsions of the active ingredient. The liquid compositions of the invention may also contain one or more corrosion inhibitors for example lauryl isoquinolinium bromide.

Surface active agents may be of the cationic, anionic or non-ionic type. Suitable agents of the cationic type include for example quaternary ammonium compounds, for example cetyltrimethyl ammonium bromide. Suitable agents of the anionic type include for example soaps, salts of aliphatic mono-esters of sulphuric acid, for example sodium lauryl sulphate; and salts of sulphonated aromatic compounds, for example dodecylbenzenesulphonate, sodium, calcium and ammonium lignosulphonate, butylnaphthalene sulphonate, and a mixture of the sodium salts of diisopropyl- and triisopropylnaphthalenesulphonic acid. Suitable agents of the non-ionic type include, for example, the condensation products of ethylene oxide with fatty alcohols such as oleyl alcohol and cetyl alcohol, or with alkyl phenols such as octyl-phenol, nonylphenol, and octylcresol. Other non-ionic agents are the partial esters derived from long chain fatty acids and hexitol anhydrides, for example sorbitol monolaurate; the condensation products of the said partial esters with ethylene oxide and the lecithins.

The compositions which are to be used in the form of aqueous solutions, dispersions or emulsions are generally supplied in the form of a concentrate containing a high proportion of the active ingredient, the concentrate being diluted with water before use. These concentrates are usually required to withstand storage for prolonged periods and after such storage to be capable of dilution with water in order to form aqueous preparations which remain homogenous for a sufficient time to enable them to be applied by conventional spray equipment.

The compositions of the invention may contain, in addition to carriers and surface-active agents, various other constituents to increase their usefulness. They may contain, for example, buffering salts to maintain the pH of the composition within a desired range; antifreeze agents, for example urea or propylene glycol; adjuvants, for example oils and humectants; and sequestrants, for example citric acid and ethylenediaminetetracetic acid, which help to prevent the formation of insoluble precipitates when the compositions are diluted with hard water. Aqueous dispersions may contain anti-settling agents and anti-caking agents. The compositions may in general contain a dye or pigment to impart a characteristic colour. Agents for increasing viscosity may be added to reduce the formation of fine droplets during spraying, and thereby reduce spray drift. Other additives useful for particular purposes will be known to those skilled in the formulation art.

In general concentrates may conveniently contain from 10 to 85% and preferably from 25 to 60% by weight of active ingredient. Dilute preparations ready for use may contain varying amounts of the active ingredient, depending upon the purpose for which they are to be used; however, dilute preparations suitable for many uses contain between 0.01% and 10% and preferably between 0.1% and 1% by weight of the active ingredient.

The invention further provides processes for preparing compounds of formula (I) above. Thus, compounds wherein $R^2$ is hydrogen may be prepared, for example, by the process of Scheme A below:

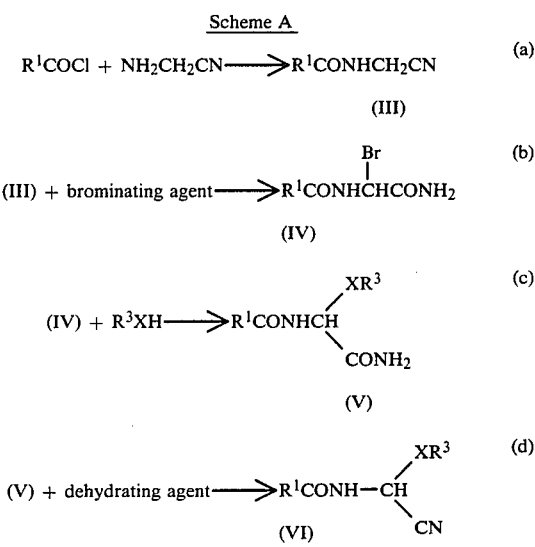

The process outlined in Scheme A begins with step (a), in which an acid chloride $R^1COCl$ is reacted with aminoacetonitrile by a conventional procedure to obtain the acylaminoacetonitrile derivative (III). This is then reacted in step (b) with a brominating agent (for example bromine in glacial acetic acid) to give the brominated derivative (IV). This bromination procedure also simultaneously hydrates the cyano group to a carbamoyl group $-CONH_2$, and necessitates treatment with a dehydrating agent at a later stage to convert the carbamoyl group back into a cyano group. It may be possible to avoid the undesired conversion of the cyano group to carbamoyl be use of a different solvent or brominating agent and thereby shorten the process by making step (d) unnecessary.

In step (c), the bromo compound (IV) is reacted with an appropriate alcohol, thiol, or amine of formula $R^3XH$ to obtain the carbamoyl compound (V). Preferably the reaction is carried out in a solvent; the solvent should be an aprotic solvent to avoid reaction of the solvent with the bromo-compound (IV). Preferably an acid acceptor is present in at least a stoichiometric proportion. Examples of acid acceptors include tertiary amines, for example triethylamine and pyridine. The reaction takes place readily even at ambient temperatures but may be accelerated if desired by heating for example to 100° C. or above.

The intermediate compounds of formula IV and V are novel and constitute a further aspect of the present invention.

The final step (d) of Scheme A is the treatment of the carbamoyl compound (V) with a dehydrating agent to convert it to the corresponding cyano compound. The dehydrating agent may be, for example, a bi-molar amount of p-toluene sulphonyl chloride in pyridine as solvent and acid acceptor, or another dehydrating agent, for example phosphorus oxychloride-demethylformamide. The reaction with p-toluenesulphonyl chloride proceeds readily at ambient temperature. Scheme A has been described in terms of brominated compounds; however, the scheme could equally be carried out using a chlorinating agent (e.g. gaseous chlorine) in place of a brominating agent, to produce the chlorinated compound corresponding to compound (IV); this could then be used in step (c) in place of compound (IV). This route cannot be used where $R^1$ is readily attacked by elemental bromine or chlorine.

A further process for making compounds of the invention in which $R^2$ is hydrogen is outlined in Scheme B:

Scheme B $R^1CONH_2 + HCO-CO_2R^6 \longrightarrow R^1CONH-CH(OH)CO_2R^6$ (a)

(VII)

$(VII) + SOCl_2 \longrightarrow R^1CONHCH(Cl)CO_2R^6$ (b)

(VIII)

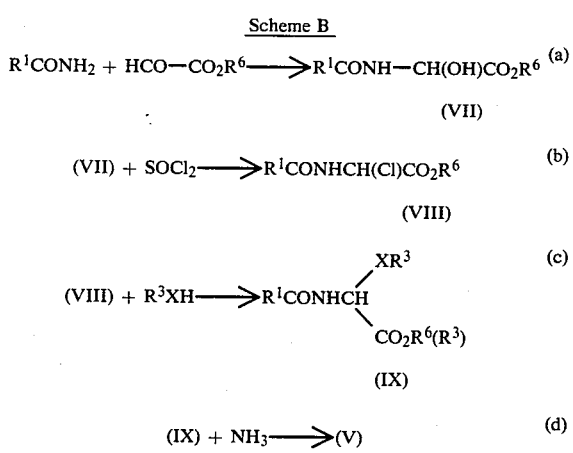

(IX) + NH₃ ⟶ (V)   (d)

In step (a) of Scheme B, an amide $R^1CONH_2$ is condensed with a glyoxylic ester $HCO-CO_2R^6$ to give the hydroxy intermediate (VII). The group $R^6$ is an ester radical, for example an alkyl group of 1 to 4 carbon atoms (e.g. a methyl group). In step (b), the hydroxy intermediate (VII) is treated with a chlorinating agent (e.g. thionyl chloride) to convert it to the chloroderivative (VIII). This is in turn reacted in step (c) with the appropriate alcohol, thiol, or amine $R^3XH$ to give the ester (IX). Treatment of this with ammonia in step (c) gives the carbamoyl derivative (V) which may then be converted to the cyano compound of the invention by the method of step (d) of Scheme A.

An alternative process for preparing the amide derivatives of the invention when X=O in formula I is a variation of the Scheme B process above. This Scheme B variation is outlined below:

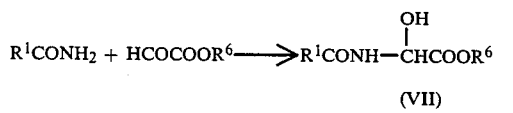

(VII)

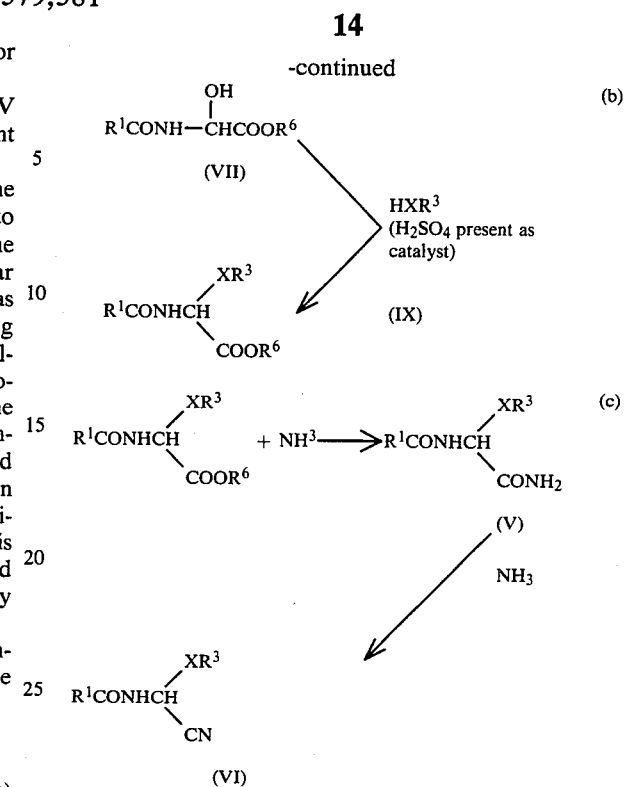

In this modified Scheme B procedure it can be seen that one can proceed directly from the hydroxy intermediate (VII) to the ester (IX) in one step. The ester (IX) is then treated with ammonia, as in step d, to produce the carbamoyl derivative (V) which in turn is converted to the cyano compound of the invention (VI) by means of the final step (step d) of the process of Scheme A.

A further process for preparing compounds of the invention in which the group $XR^3$ is an $-NHCOR^3$ group is outlined in Scheme C below.

Scheme C $R^1CONHCH(Br)CONH_2 +$   (a)

(IV)

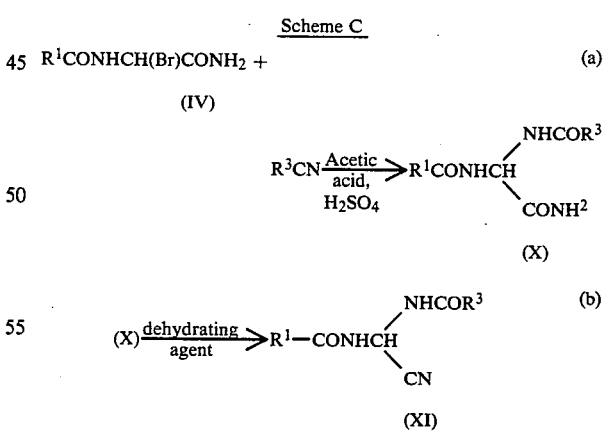

According to Scheme C the bromo-amide (IV) (prepared as in Scheme A) is reacted with the appropriate nitrile $R^3CN$ in acetic acid under the conditions of the Ritter reaction to give the amide (X). This is then treated with a dehydrating agent (e.g. trifluoroacetic anhydride in pyridine) to give the required nitrile (XI).

A further method of preparing the nitriles (XI) is shown in Scheme D below.

Scheme D

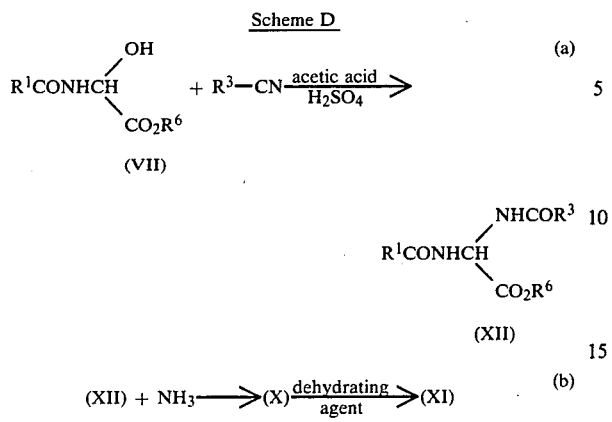

In Scheme D, the hydroxy-ester (VII) prepared as in Scheme B is reacted with the appropriate nitrile $R^3CN$ in the presence of acetic acid and sulphuric acid (Ritter reaction) to give the amide (XII). This may then be reacted with ammonia to give the amide (X) already prepared in Scheme C. As in Scheme C the amide (X) may then be dehydrated to give the required nitrile (XI). The conversion of (XII) to (X) may be troublesome because the esters (XII) tend to be highly insoluble.

A further method of preparing compounds of the invention is outlined in Scheme E.

Scheme E

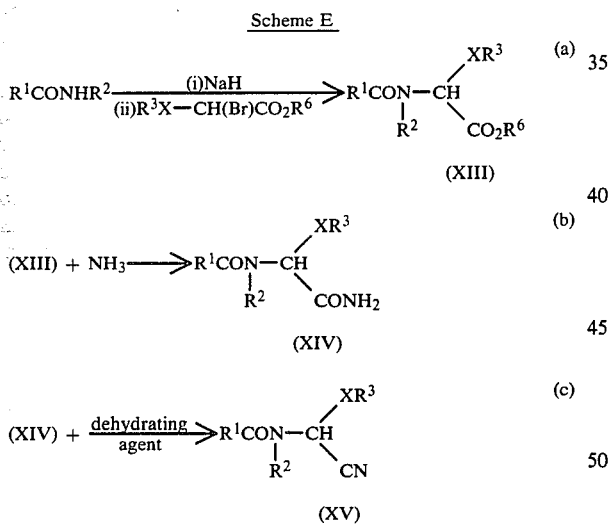

According to Scheme E, and amide $R^1CONHR^2$ is first treated with sodium hydride and the anion so generated is then reacted with an alpha bromo ester $R^3X$—$CH(Br)CO_2R^6$ to give the ester (XIII). This is then reacted with ammonia to give the amide (XIV), and finally (XIV) is treated with a dehydrating agent to give the nitrile (XV).

This method may conveniently be used to prepare compounds in which $R^2$ is other than hydrogen, particularly when either $R^1$ or $R^2$ is susceptible to reaction with bromine or sulphuryl chloride, which are used as reagents in certain other routes described herein.

A further method for preparing compounds of the invention is outlined in Scheme F.

Scheme F

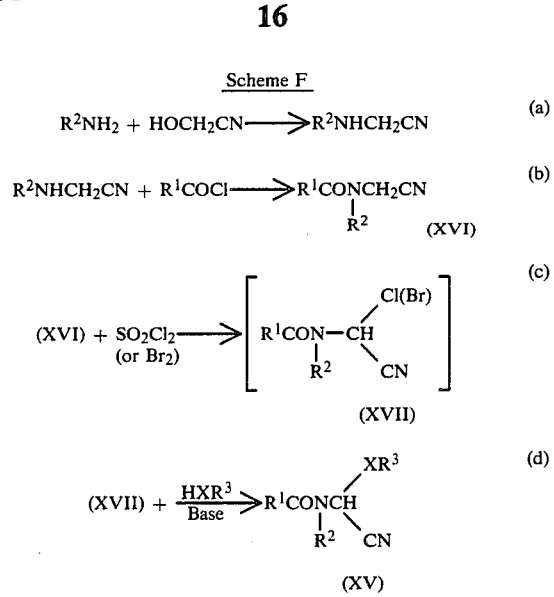

According to Scheme F, an amine $R^2NH_2$ is condensed with formaldehyde cyanhydrin to give the substituted aminoacetonitrile $R^2NHCH_2CN$. This is then acylated by the appropriate acid chloride $R^1COCl$ to give the amide derivative (XVI).

This in turn is chlorinated (e.g. with $SO_2Cl_2$) or brominated (e.g. with $Br_2$) to give the highly reactive bromo- or chloro-derivative (XVII). This is treated with the appropriate alcohol, thiol or amine $R^3XH$ in the presence of base to give the required nitrile (XV).

The chloro- or bromo-nitriles (XVII) are too unstable to be isolated and characterised, and are used within a short time after they are prepared. The final stage (d) of the scheme may conveniently be carried out by using an excess of the alcohol, thiol, or amine $R^3XH$ as solvent, and anhydrous potassium carbonate as the base. Triethylamine or other tertiary amines may also be used as the base.

The cyanoamides (XVI) may also be prepared by methods other than that described above. Thus, the $R^2$ substituent may be introduced by alkylation as shown below:

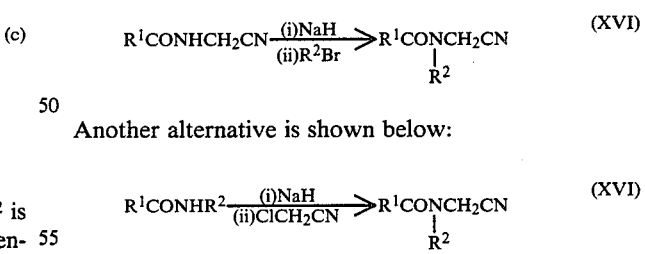

Another alternative is shown below:

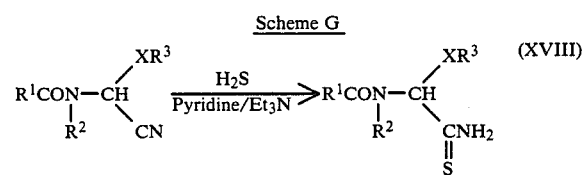

Compounds of the invention in which the group E is a thiocarbamoyl radical may be prepared according to Scheme G below:

Scheme G $$R^1CON-CH\begin{matrix}XR^3\\ \\ \end{matrix} \quad \xrightarrow[\text{Pyridine/Et}_3N]{H_2S} \quad R^1CON-CH\begin{matrix}XR^3\\ \\ CNH_2\\ \parallel\\ S\end{matrix} \quad (XVIII)$$

The reaction is conveniently carried out by passing gaseous H₂S through a solution of the nitrile in pyridine containing a little triethylamine as catalyst. Usually the solution is externally cooled to 0-10°. If the product does not separate from the solution, it may be isolated by removal of the solvent.

The amide derivatives of formula I, and compositions containing them, are variously active against a wide range of fungal diseases, particularly, for example, against:

Plasmopara viticola (downy mildew) on vines and
Phytophthora infestans (late blight) on potatoes and tomatoes and other species of Phytophthora
Phytophthora parasitica, Phytophthora cinnamomi, Phytophthora palmivora and Phytophthora capsici on a range of commercially important crops
Peronospora tabacina on tobacco
Peronospora parasitica on cabbage
Peronospora destructor on onions
Bremia lactuca on lettuce
Phythium species on a range of commercially important crops
Other fungal diseases, for example:
Venturia inaequalis (scab) on apples
Cercospora arachidicola on peanuts and other Cercospora species.

A particularly valuable feature of the activity of the amide derivatives is their systemic effect, i.e. their ability to move in a plant to combat an infection or infestation remote from the site of initial application. Thus a derivative, or a composition containing it, may be applied to the soil surrounding the roots of a plant or to the seed or to other plant areas, e.g. leaves, and be taken up by the plant through its roots, or other areas, to combat fungi locally or elsewhere on the plants.

In another aspect, therefore, the invention provides a process for combatting fungi, especially of inhibiting the growth of fungi on plants, which comprises applying to the plants, or the locus thereof, a fungicidally effective amount of a compound of the formula (I) as hereinbefore defined. The amount of the compound may vary, depending upon the identity of the particular compound chosen, the fungal species whose growth is to be inhibited, and the plant or locus involved. The skilled worker in the fungicide art will readily be able to establish appropriate application rates by standard procedures without undue experimentation.

Preferred compounds for use in the fungicidal compositions of the invention and the process for combatting fungi are those defined in detail above with reference to formula I wherein $R_2$ is hydrogen, $R^1$ is optionally-substituted phenyl, or heterocyclyl, for example 2-furyl, X is O or S (X is preferably O) and $R^3$ is alkyl, alkenyl, or haloalkyl, and E is CN or $CSNH_2$.

Preferred phenyl substitution, when $R^1$ is phenyl, is at the 3, 4 or 5 positions and is alkyl, alkoxy, methylenedioxy or halogen. Preferred alkyl groups for $R^3$ are $C_{1-4}$ alkyl. Allyl is also a preferred group for $R^3$.

The compounds used in the process and compositions of the invention are preferably applied in the form of a composition, in which the active ingredient is mixed with a carrier comprising a solid or liquid diluent. In another aspect, therefore, the invention provides a fungicidal composition, comprising as an active ingredient a compound of the formula (I) as hereinbefore defined, in admixture with a solid or liquid diluent. Preferably the composition also comprises a surface-active agent.

The amide derivatives may be used as such for antifungal purposes but are more conveniently formulated into compositions for such usage.

The invention also provides fungicidal compositions comprising as active ingredient an amide derivative as defined in any of the paragraphs above.

The amide derivatives and compositions containing them can be used to combat plant fungi and treat plants or seeds in a number of ways, for example they can be applied, formulated or unformulated, directly to the foliage of a plant which is infected or likely to become infected, or they can be applied also to bushes and trees, to soil or to other medium in which plants, bushes or trees are growing or to be planted, or they can be sprayed on, dusted on or applied as a cream or paste formulation. Application can be to any part of the plant, bush or tree, for example to the foliage, stems, branches, seeds or roots, or to the soil surrounding the roots.

The terms "combatting" and "treatment" as used herein embrace all the foregoing modes of application and the term "plant" includes seedlings, bushes and trees. Furthermore, the method of the invention includes protectant, prophylactic and eradicant treatment.

The derivatives are preferably used for agricultural and horticultural purposes in the form of compositions. The type of composition used in any instance will depend upon the particular purpose envisaged.

The compositions may be in the form of dusting powders or granules, for example ordinary grains or "slow release" granules wherein the active ingredient is mixed with a solid diluent or carrier, for example, kaolin, bentonite, kieselguhr, dolomite, calcium carbonate, talc, powdered magnesia, Fuller's earth, gypsum, Hewitt's earth, diatomaceous earth and China clay. Compositions for dressing seed may, for example, comprise an agent (for example a mineral oil) for assisting the adhesion of the composition to the seed.

The compositions may also be in the form of dispersible powders or grains comprising a wetting agent to facilitate the dispersion in liquids of the powder or grains which may contain also fillers and suspending agents.

The aqueous dispersion of emulsions may be prepared by dissolving the active ingredient(s) in an organic solvent which may contain wetting, dispersing or emulsifying agent(s) and then adding the mixture so obtained to water which may also contain wetting, dispersing or emulsifying agent(s). Suitable organic solvents are ethylene dichloride, isopropyl alcohol, propylene glycol, diacetone alcohol, toluene, kerosene, methylnaphthalene, xylenes and trichloroethylene.

The compositions for spraying may also be in the form of aerosols wherein the formulation is held in a propellant, e.g. fluorotrichloromethane or dichlorodifluoromethane.

By including suitable additives, for example additives for improving the distribution, adhesive power and resistance to rain on treated surfaces, the different compositions can be better adapted for various utilities.

The derivatives can be used in smoke generators and also as mixtures with fertilisers (e.g. nitrogen- or phosphorus-containing fertilisers). Compositions comprising only granules of fertiliser incorporating, for example coated with, the derivative, are preferred.

The invention therefore also provides a fertiliser composition comprising the derivative and a fertiliser.

The compositions may also be in the form of liquid preparations for use as dips or sprays which are generally aqueous dispersions or emulsions containing the active ingredient in the presence of one or more surface active agent(s), dispersing agent(s), emulsifying agent(s) or anionic or non-ionic agents. Suitable cationic agents are quaternary ammonium compounds for example, cetyltrimethylammonium bromide.

Suitable anionic agents are soaps, salts of aliphatic monoesters of sulphuric acid (for example sodium lauryl sulphate), and salts of sulphonated aromatic compounds (for example sodium dodecylbenzene-sulphonate, sodium, calcium or ammonium lignosulphonate, butylnaphthalene sulphonate, and a mixture of sodium di-isopropyl- and triisopropylnaphthalene sulphonates).

Suitable non-ionic agents are the condensation products of ethylene oxide with fatty alcohols such as oleyl alcohol or cetyl alcohol, or with alkyl phenols such as octylphenol, nonylphenol and octylcresol. Other non-ionic agents are the partial esters derived from long chain fatty acids and hexitol anhydrides, the condensation products of the said partial esters with ethylene ocide, and the lecithins. Suitable suspending agents are hydrophilic colloids (for example polyvinylpyrrolidone and sodium carboxymethylcellulose), and the vegetable gums (for example gum acacia and gum tragacanth).

The compositions for use as aqueous dispersions or emulsions are generally supplied in the form of a concentrate containing a high proportion of the active ingredients), the concentrate to be diluted with water before use. These concentrates often should be able to withstand storage for prolonged periods and after such form aqueous preparations which remain homogenous for a sufficient time to enable them to be applied by conventional spray equipment. The concentrates may conveniently contain 10-85%, generally 25-60%, by weight of the active ingredient(s).

When diluted to form aqueous preparations, such preparations may contain varying amounts of the active ingredient(s) depending upon the intended purpose, but an aqueous preparation containing 0.0005% or 0.01% to 10% by weight of active ingredient(s) may be used.

The compositions of this invention can comprise also other compound(s) having biological activity, e.g. compounds having similar or complementary fungicidal or plant growth regulating activity or compounds having herbicidal or insecticidal activity.

The other fungicidal compound can be for example one which is capable of combating ear diseases of cereals (e.g. wheat) such as Septoria, Gibberella and Helminthosporium spp., seed and soil borne diseases and downy and powdery mildews on grapes and powdery mildew and scab on apple etc. These mixtures of fungicides can have a broader spectrum of activity than the compound of general formula (I) alone; further the other fungicide can have a synergistic effect of the fungicidal activity of the compound of general formula (I). Examples of the other fungicidal compound are imazalil, benomyl, carbendazim (BCM), thiophanate-methyl, captafol, captan, sulphur, dithiocarbamates, carbathiins, copper oxychloride, triforine, dodemorph, tridemorph, dithianon, pyrazophos, binapacryl, quinomethionate, panoctine, furalaxyl, aluminium tris(ethylphosphonate), DPX3217, ethirimol, dimethirimol, bupirimate, chlorothalonil and metazanine.

Suitable insecticides are pirimor, croneton, dimethoate, metasystox and formothion.

The other plant growth regulating compound can be one which controls weeds or seedhead formation, improves the level or longevity of the plant growth regulating activity of the compounds of general formula (I), selectively controls the growth of the less desirable plants (e.g. grasses) or causes the compound of general formula (I) to act faster or slower as a plant growth regulating agent. Some of these other agents will be herbicides. Examples of suitable agents are the gibberellins (e.g. $GA_3$, $GA_4$ or $GA_7$), the auxins (e.g. indoleacetic acid, indolebutyric acid, naphthoxyacetic acid or naphthylacetic acid), the cytokinins (e.g. kinetin, diphenylurea, benzimidazole, benzyladenine or BAP), phenoxyacetic acids (e.g. 2,4-D or MCPA), substituted benzoic acids (e.g. TIBA), morphactins (e.g. chlorfluorecol), maleic hydrazide, glyphosate, glyphosine, long chain fatty alcohols and acids (e.g. Off Shoot O or Off Shoot T), dikegulac, Sustar, Embark, substituted quaternary ammonium and phosphonium compounds (e.g. CCC or Phosfon-D), Ethrel, carbetamide, Racuza, Alar, asulam, abscissic acid, isopyrimol, RH531, hydroxybenzonitriles (e.g. bromoxynil), Avenge, Suffix or Lontrel.

The invention is illustrated by the following Examples, in which unless otherwise stated all parts are by weight and temperatures in degrees Centigrade. The Examples that describe chemical syntheses give details in some cases of the nuclear magnetic resonance (NMR) spectra of the compounds. The information given is the chemical shift ($\delta$) for each peak in the spectrum together with a symbol to indicate the nature of the peak, as follows:- s(singlet); d(doublet); m(multiplet); q(quartet); t(triplet). The solvent used was fully deuterated dimethyl sulphoxide or deuterochloroform ($CDCl_3$).

EXAMPLE 1

This Example illustrates the preparation of compound no. 4 of Table I by the process of Scheme A.

(a) Preparation of Benzoylamino(bromo)acetamide

To a suspension of benzoylaminoacetonitrile (5 g) in stirred glacial acetic acid (50 ml) was added all at once bromine (5.0 g). After a brief induction period, the bromine colour was discharged and the product (5.8 g) precipitated from the acetic acid. The product was filtered off, washed with glacial acetic acid, and then with anhydrous ether, and dried. A sample crystallised from glacial acetic acid had m.p. 157° (dec.).

Found: C, 42.22; H, 3.7; N, 10.81 $C_9H_9BrN_2O_2$; requires: C, 42.02; H, 3.5; N, 10.89%.

(b) Preparation of Benzoylamino(ethoxy)acetamide

The foregoing bromoamide (13.4 g) was suspended in anhydrous ethanol (50 ml) and heated on a steam bath just long enough for it to dissolve (ca. 5 min), whereupon the solution was cooled. The ethanol was removed under vacuum and the residual heavy oil was dissolved in water (40 ml) and neutralised by the cautious addition of solid sodium bicarbonate. The solution was then extracted with chloroform (200 ml) and the dried ($MgSO_4$) extract evaporated to yield a white solid. Crystallisation of this from dichloromethane-hexane gave the product (7.7 g), m.p. 148°–150°.

Found: C, 59.19; H, 6.27; N, 12.5 $C_{11}H_{14}N_2O_3$; requires: C, 59.45; H, 6.34; N, 12.6% $\delta$(DMSO-$d_6$): 1.15 (t, 3H), 3.55 (q, 2H), 5.55 (d, 1H), 7.2–8.0 (m, 7H), 9.0 (d, 1H).

(c) Preparation of Benzoylamino(ethoxy)acetonitrile
(Compound No. 4)

A solution of the foregoing ethoxyamide (5.55 g) in anhydrous pyridine (40 ml) containing p-toluenesulphonyl chloride (4.78 g) was kept at room temperature for 72 hours. The reaction mixture was diluted with water (200 ml) and the precipitated solid filtered off, washed with water and dried. Crystallisation of the solid from carbon tetrachloride gave the product (2.5 g), m.p. 107°–110°.

Found: C, 64.31; H, 6.3; N, 13.54 $C_{11}H_{12}N_2O_2$; requires: C, 64.69; H, 5.92; N, 13.71% $\delta(CDCL_3)$: 1.25 (t, 3H), 3.8 (q, 2H), 6.3 (d, 1H), 7.4–8.0 (m, 6H).

EXAMPLE 2

This Example illustrates the preparation of compound no. 38 of Table I by the process of Scheme B.

(a) Preparation of Methyl-[3-Methoxybenzoylamino(hydroxy)]acetate

3-Methoxybenzamide (13.25 g) and methyl glyoxylate (7.72 g) in toluene (150 ml) were heated under reflux in a Dean-Stark apparatus for 6 hours. On cooling the mixture the product separated and was crystallised from toluene. Yield, 12.0 g, m.p. 93°–94°.

Found: C, 55.45; H, 5.37; N, 6.3 $C_{11}H_{13}NO_5$; requires: C, 55.23; H, 5.43; N, 5.85%.

(b) Preparation of 3-Methoxybenzoylamino(ethoxy)acetamide

The foregoing ester (5.0 g) and thionyl chloride (40 ml) were stirred together for 2 hours., after which the excess of thionyl chloride was removed under vacuum. The residue was dissolved in ethanol (100 ml) and the solution then evaporated under vacuum. The residual oil was treated with aqueous ammonia (d 0.88) and the mixture allowed to stand. The solid so formed was filtered off, dried, and crystallised from chloroform-light petroleum to give the product (1.8 g), m.p. 143°–144°.

Found: C, 56.17; H, 6.49; N, 10.73 $C_{12}H_{16}N_2O_4$; requires: C, 57.14; H, 6.35; N, 11.11% $\delta(DMSO-d_6)$: 1.3 (t, 3H), 3.7 (q, 2H), 4.0 (s, 3H), 5.7 (d,1H), 7.2–7.8 (m, 6H), 9.15 (d, 1H).

(c) Preparation of 3-Methoxybenzoylamino(ethoxy)acetonitrile

The foregoing ethoxyamide (1.0 g), p-toluenesulphonyl chloride (1.28 g) and pyridine (20 ml) were allowed to stand at room temperature for 72 hrs. The reaction was then worked up as described in paragraph (c) of Example 1. The product (0.7 g) was crystallised from chloroform-light petroleum and had m.p. 72°.

$\delta(CDCl_3)$: 1.2 (t, 3H), 3.7 (q, 2H), 3.8 (s, 3H), 6.2 (d, 1H), 7–7.6 (m, 5H).

EXAMPLE 3

This Example illustrates the preparation of compound no. 53 of Table 1, using the process of Scheme F.

Preparation of N-Methylbenzoylamino(methoxy)acetonitrile

To a cooled (5°–10°) and stirred solution of N-methylbenzoylaminoacetonitrile (5.0 g) in anhydrous carbon tetrachloride (75 ml) was added dropwise bromine (4.6 g). Following the addition the mixture was stirred for a further 5 min. at room temperature, when methanol (25 ml) was added all at once. After stirring the mixture for a further 5 min., triethylamine (5.81 g) was added to the mixture. The solution was then washed with water and the organic phase dried ($MgSO_4$) and evaporated. The residual oil was chromatographed on a dry silica column using ether-hexane (7:3) as an eluent. Separation of the major band from the column gave the product as a colourless oil (1.0 g) $n_D^{21}$ 1.5233.

$\delta(CDCl_3)$: 3.1 (s, 3H), 3.4 (s, 3H), 6.0 (very broad, 1H), 7.4 (s, 5H).

EXAMPLE 4

This Example illustrates the preparation of compound no. 40 of Table I, using the process of Scheme A.

(a) Preparation of 3-Chlorobenzoylamino(methylthio)acetamide

To a solution of 3-chlorobenzoylamino(bromo)acetamide (5.5 g) in anhydrous tetrahydrofuran (100 ml) containing methyl mercaptan (slight excess) was added 1 equivalent of triethylamine and the mixture kept for 72 hrs. The solution was filtered and the filtrate evaporated to give an oil which solidified on treatment with ether. Crystallisation of the solid from ethyl acetate gave the product (0.67 g).

$\delta(DMSO-d_6)$: 2.06 (s, 3H), 5.6 (d, 1H), 7.4–7.8 (m, 6H), 8.9 and 9.2 (two doublets, 1H).

(b) Preparation of 3-chlorobenzoylamino(methylthio)acetonitrile
(Compound No. 40)

The foregoing amide (0.67 g) and 2 equivalents of p-toluenesulphonyl chloride in pyridine (10 ml) were kept at room temperature for 48 hrs. The mixture was then poured into water (100 ml). The solid which separated was dried, and crystallised from chloroform-light petroleum to give the product (0.1 g), m.p. 115°–117°.

Found: C, 48.99; H, 3.71; N, 11.01 $C_{10}H_9ClN_2OS$; requires: C, 49.9; H, 3.77; N, 11.64% $\delta(CDCl_3)$: 2.35 (s, 3H), 6.05 (d, 1H), 7.8–7.2 (m, 5H).

EXAMPLE 5

This Example illustrates the preparation of compound no 158 of Table 1 by the process of Scheme C.

(a) Preparation of Acetylamino(3,5-dimethylbenzoylamino)acetamide

To a suspension of 3,5-dimethylbenzoylaminoacetonitrile (1 g) in glacial acetic acid (20 ml) was added all at once bromine (0.85 g). After stirring the mixture at room temperature for 15 min. the white solid was separated, washed with anhydrous ether and then re-suspended in glacial acetic acid (10 ml). To this was added concentrated sulphuric acid (1.5 ml) and acetonitrile (8 ml). After 1 hour the mixture was poured into water (30 ml) and extracted with chloroform (2×30 ml). The dried ($MgSO_4$) extract was evaporated and the residue crystallised from aqueous ethanol to give the product (0.38 g) as a white solid (Compound No 154 of Table I), m.p. 244°–5°.

Found: C, 58.49; H, 6.42; N, 15.46 $C_{13}H_{17}N_3O_3$; requires: C, 59.13; H, 6.46; N, 15.97% $\delta(DMSO-d_6)$: 1.9 (3H,s), 2.3 (6H,s), 5.8 (1H,dd), ca. 7.1–7.5 (5H,m), 8.3 (1H,d), 8.7 (1H,d).

(b) Preparation of Acetylamino (3,5-dimethylbenzoylamino)acetonitrile

The foregoing acetamide (1.0 g) was dissolved in anhydrous pyridine (25 ml) which was then cooled to −25°. Trifluoroacetic anhydride (1.5 g) was added dropwise to the cooled and stirred solution, and following the addition the solution was allowed to come to 0° whereupon it was poured into water (70 ml) and extracted with ether (2×50 ml). Evaporation of the ethereal extracts and crystallisation of the residue from ethyl acetate-hexane gave the product (0.6 g) as a pale cream solid, m.p. 195°-7°.

Found: C, 62.51; H, 5.98; N, 17.16 $C_{13}H_{15}N_3O_2$; requires: C, 63.67; H, 6.12; N, 17.14% δ(DMSO-$d_6$): 1.8 (3H,s), 2.2 (6H,s), 6.2 (1H,dd), 7.1 (1H,s), 7.4 (2H,s), 9.1 (1H,s), 9.5 (1H,s).

EXAMPLE 6

This Example illustrates the preparation of compound no. 153 of Table I by the process of Scheme D.

(a) Preparation of Methyl Acetylamino (3,5-dichlorobenzoylamino)acetate

A mixture of 3,5-dichlorobenzamide (19.0 g) and methyl glyoxylate (8.8 g) in ethyl acetate (300 ml) was heated under reflux for 8 hours. The solvent was removed and the residual adduct was crystallised from chloroform-light petroleum. A portion (4.0 g) of the adduct was dissolved in a mixture of glacial acetic acid (30 ml) and acetonitrile (10 ml) with stirring, and then concentrated sulphuric acid (4 ml) was added. The mixture was kept at room temperature overnight when water (100 ml) was added. The precipitated solid was washed with water, dried, and crystallised from ethanol to give the product (2.45 g) as a colourless crystalline solid, m.p. 235°-237°.

Found: C, 45.24; H, 3.88; N, 8.84 $C_{12}H_{12}Cl_2N_2O_4$; requires: C, 45.14; H, 3.76; N, 8.77% δ(DMSO-$d_6$): 1.95 (3H,s), 3.7 (3H,s), 5.9 (1H,dd), 7.95 (3H,m), 8.9 (1H,d), 9.75 (1H,d).

(b) Preparation of Acetylamino (3,5-dichlorobenzoylamino)acetamide

The foregoing ester (1.46 g) was dissolved in dimethylformamide (70 ml) which was then saturated with ammonia (gas) and the mixture kept for 7 days. The solvent was removed under reduced pressure and the residue crystallised from aqueous dimethylformamide to give the product (0.72 g), m.p. 267°-268° (dec).

Found: C, 43.62; H, 3.72; N, 13.82 $C_{11}H_{11}Cl_2N_3O_3$; requires: C, 43.42; H, 3.62; N, 13.82% δ(DMSO-$d_6$): 1.95 (3H,s), 5.9 (1H,dd), 7.3 (2H,d,broad) 7.6 (1H,m), 7.9 (2H,m), 8.35 (1H,d), 9.2 (1H,d).

(c) Preparation of Acetylamino (3,5-dichlorobenzoylamino)acetonitrile

The foregoing acetamide (0.5 g) in anhydrous pyridine (10 ml) at −25° was treated with trifluoroacetic anhydride as described above. The product (0.18 g), crystallised from aqueous dimethylformamide, had m.p. 227°-228°.

Found: C, 45.95; H, 3.12; N, 14.43 $C_{11}H_9Cl_2N_3O_2$; requires: C, 46.15; H, 3.15; N, 14.68% δ(DMSO-$d_6$): 1.95 (3H,s), 6.4 (1H,dd), 7.9 (3H,m), 9.35 (1H,d), 10.0 (1H,d).

EXAMPLE 7

This Example illustrates the preparation of compound no. 159 of Table I by the process of Scheme E.

(a) N-Furfuryl-3,5-dichlorobenzamide

To a vigorously stirred solution of furfurylamine (2.78 g) in ethyl acetate (40 ml) was added sodium hydroxide (1.15 g) in water (45 ml), followed immediately by the addition of a solution of 3,5-dichlorobenzoyl chloride (6.0 g) in ethyl acetate (20 ml). Following the mild exothermic reaction the ethyl acetate layer was removed, dried ($MgSO_4$), and evaporated. Crystallisation of the residue from cyclohexane gave the product (6.6 g) as colourless needles.

(b) Preparation of N-Furfuryl-3,5-dichlorobenzoylamino(methoxy)acetonitrile To a stirred suspension of sodium hydride (0.58 g) in anhydrous tetrahydrofuran (40 ml) was added in portions the foregoing amide (3.0 g). Following the addition and cessation of hydrogen evolution was added with stirring methyl 2-bromo-2-methoxy acetate (2.04 g) and the mixture stirred for a further 2 hours at room temperature. Water (100 ml) was then added and the solution extracted with methylene chloride (3×50 ml) and the extracts dried and evaporated. The resultant crude oily ester was dissolved in methanol (20 ml) which was then saturated with ammonia gas and kept overnight. The solvent was removed under reduced pressure and the residual oil triturated with ether to give crude amide (1.91 g). The crude amide (1.75 g) was dissolved in anhydrous pyridine (10 ml), cooled to 0° with stirring and phosphorus oxychloride (0.84 g) added dropwise so that the temperature of the mixture did not exceed 0°. After 25 minutes at 0°, water (100 ml) was added and the mixture was extracted with ether (40 ml). The dried ($MgSO_4$) ether extract was chromatographed on silica using diisopropyl ether as the eluent. Following elution from the column and evaporation of the solvent the product (1.24 g) was obtained as a colourless oil which slowly crystallised, m.p. 89°-90°.

δ($CDCl_3$): 3.4 (3H,s), 4.65 (2H,s), 6.1 (1H,s,broad) 6.3 (2H,m), 7.3-7.5 (4H,m).

EXAMPLE 8

This Example illustrates the preparation of compound no. 142 of Table I by the process of Scheme F.

Preparation of N-Benzyl-3,5-dimethylbenzoylamino(methoxy)acetonitrile

To a stirred solution of glycollonitrile (25 g) in methanol was added dropwise over 45 minutes benzylamine (46.9 g) keeping the temperature of the reaction between 15°-20°. Following the addition the reaction mixture was kept overnight at room temperature, and then distilled to give benzylaminoacetonitrile (42.0 g) as a colourless oil, b.p. 120°/15 mm. Reaction of this (3.0 g) with 3,5-dimethylbenzoyl chloride (3.46 g) was described above gave crude N-benzyl-3,5-dimethylbenzoylaminoacetonitrile (5.81 g) as a colourless viscous oil which was used in the next stage without further purification. To this crude amide (2.0 g) in anhydrous methylene chloride (8 ml) was added sulphuryl chloride (0.97 g). Following the cessation of gas evolution (ca. 15 min.), anhydrous methanol (20 ml) and finely powdered anhydrous potassium carbonate (1.95 g) was added to the mixture which was then stirred for 30 minutes. Solids were removed from the solution which was then evaporated and the residual oil chromatographed on a column of silica using methylene chloride as an eluent. Following elution from the column and evaporation of the solvent, the product (1.2 g) was obtained as a very pale-yellow viscous oil.

Found: C, 73.87; H, 6.67; N, 9.22 $C_{19}H_{20}N_2O_2$; requires: C, 74.02; H, 6.49; N, 9.09%

($CDCl_3$): 2.28 (6H,s), 3.25 (3H,s), 4.75 (2H,s), 5.85 (1H,s,broad), ca. 7.0–7.4 (8H,m).

EXAMPLE 9

This Examples illustrates the preparation of compound no. 84 of Table I by the process of Scheme G.

Preparation of 3-chlorobenzoylamino(ethoxy)thioacetamide

Into a solution of 3-chlorobenzoylamino(ethoxy) acetonitrile (1 g) in toluene (50 ml) containing triethylamine (1 g) was passed hydrogen sulphide gas. The precipitated product (0.72 g) was collected and crystallised from chloroform-light petroleum. m.p. 136°–137°.

Found: C, 48.53; H, 4.84; N, 10.19 $C_{11}H_{18}ClN_2O_2S$; requires: C, 48.44; H, 4.80; N, 10.27%.

EXAMPLE 10

This Example illustrates the herbicidal properties of compounds of Table I. The compounds were submitted to herbicide tests as described below.

Each compound was formulated for test by mixing an appropriate amount of it with 5 ml of an emulsion prepared by diluting 160 ml of a solution containing 21.8 grams per liter of Span 80 and 78.2 grams per liter of Tween 20 in methylcyclohexanone to 500 ml with water. Span 80 is a Trade Mark for a surface-active agent comprising sorbitan monolaurate. Tween 20 is a Trade Mark for a surface-active agent comprising a condensate of 20 molar proportions of ethylene oxide with sorbitan monolaurate. The mixture of the compound and the emulsion was then shaken with glass beads and diluted to 44 ml with water. The spray composition so prepared was sprayed on to young pot plants (post-emergence test) of the species named in Tables 2 and 3 below, at a rate equivalent to 1000 liters per hectare. Damage to plants was assessed 13 days after spraying by comparison with untreated plants, on a scale of 0 to 5 where 0 is 0 to 20% damage and 5 is complete kill. In the table of results, a dash (—) means no test was made.

A test was also carried out to detect pre-emergence herbicidal activity. Seeds of the test species were placed on the surface of fibre trays of soil and were sprayed with the compositions at the rate of 1000 liters per hectare. The seeds were then covered with further soil. 20 days after spraying, the seedlings in the sprayed fibre trays were compared with the seedlings in unsprayed control trays, the damage being assessed on the same scale of 0 to 5.

The results of the tests are given in Tables 2 and 3 below.

TABLE 2

| COMPOUND NO | RATE OF APPLICATION kg/ha | PRE- OR POST-EMERGENCE APPLICATION | TEST PLANTS | | | | | | | | | | | | | | | | | | | | | | | | | | | | |
|---|---|---|---|---|---|---|---|---|---|---|---|---|---|---|---|---|---|---|---|---|---|---|---|---|---|---|---|---|---|---|---|
| | | | Sb | Rp | Ct | Sy | Mz | Ww | Rc | Sn | Ip | Am | Pi | Ca | Po | Xs | Ab | Cv | Ot/Av | Dg | Pu | St | Ec | Sh | Ag | Cn |
| 2 | 5.0 | Pre | 2 | 3 | 1 | 4 | 2 | 5 | 2 | 2 | — | 0 | 4 | — | 5 | 1 | 4 | — | 5 | 5 | 5 | 5 | 5 | 1 | 5 | 3 |
| | | Post | 2 | 2 | 0 | 2 | 4 | 4 | 2 | 0 | 1 | 4 | 4 | — | 4 | — | 2 | — | 4 | 2 | 4 | 4 | 5 | 0 | 3 | 0 |
| 4 | 1.0 | Pre | 2 | 4 | 3 | 0 | 5 | 4 | 4 | — | 4 | 4 | 4 | — | 2 | 2 | 5 | 3 | 5 | 5 | 4 | 4 | 3 | 2 | 3 | 2 |
| | | Post | 0 | 0 | 0 | 2 | 3 | 5 | 1 | 0 | 3 | 2 | 3 | 2 | 2 | 0 | 4 | — | 5 | 2 | 4 | 3 | 3 | 1 | 5 | 0 |
| 8 | 5.0 | Pre | 0 | 1 | 3 | 3 | 3 | 4 | 0 | 0 | 5 | 1 | — | 2 | 4 | 0 | — | — | 4 | 4 | 5 | 4 | 5 | 3 | 3 | 1 |
| | | Post | 0 | 0 | 0 | — | 0 | 5 | — | 0 | 0 | — | 3 | — | 2 | — | 1 | — | 2 | 3 | 4 | — | 3 | — | 3 | 2 |
| 15 | 1.0 | Pre | 0 | 0 | 0 | 0 | 0 | 4 | 0 | 0 | 0 | 0 | 3 | — | 3 | 0 | 0 | — | 2 | 0 | 3 | — | 3 | 3 | 3 | — |
| | | Post | 0 | 0 | 0 | 0 | 0 | 2 | 0 | 0 | 0 | 0 | 0 | 0 | 0 | 0 | 0 | 2 | 0 | — | 0 | 3 | 0 | 0 | 0 | 0 |
| 17 | 1.0 | Pre | 0 | 0 | 0 | 0 | 0 | 0 | 0 | 0 | 0 | 0 | 0 | 0 | 0 | 0 | — | — | 0 | — | 0 | 0 | 0 | 0 | 0 | 0 |
| | | Post | 0 | 0 | 0 | 0 | 0 | 0 | 0 | 0 | 0 | 0 | 0 | 0 | 0 | 0 | 0 | — | 0 | 1 | 1 | 0 | 1 | 0 | 0 | 0 |
| 18 | 0.2 | Pre | 4 | 4 | 0 | 4 | 0 | 5 | 4 | 4 | 3 | 3 | — | 2 | 5 | 0 | 5 | 2 | 4 | 5 | 5 | 5 | 5 | 4 | 5 | 0 |
| | | Post | 1 | 2 | 1 | 1 | 3 | 4 | 0 | 2 | 3 | 4 | — | 2 | 3 | 2 | 2 | 3 | 3 | 4 | 4 | 5 | 4 | — | 0 | 3 | 0 |
| 20 | 1.0 | Pre | 4 | 4 | 4 | 4 | 4 | 5 | 5 | 4 | 3 | 5 | — | — | 5 | 2 | 4 | 3 | 5 | 4 | 5 | 5 | 5 | 4 | 5 | 0 |
| | | Post | 1 | 2 | 0 | 0 | 5 | 4 | 0 | 2 | 3 | 0 | — | — | 3 | 2 | 0 | 3 | 4 | 4 | 5 | 4 | 4 | 0 | 5 | 0 |
| 21 | 1.0 | Pre | 0 | 0 | 0 | 0 | 0 | 5 | 0 | 0 | 3 | 3 | — | — | 0 | 2 | 3 | 3 | 3 | 5 | 3 | 5 | 4 | 4 | 3 | 0 |
| | | Post | 1 | 1 | 0 | 0 | 4 | 0 | 0 | 4 | 3 | 5 | 0 | — | — | 2 | 0 | — | 2 | 4 | 5 | 4 | 5 | — | 2 | 3 | 0 |
| 22 | 0.2 | Pre | 0 | 0 | 0 | 4 | 0 | 5 | 4 | 4 | 4 | 5 | — | 3 | 0 | 2 | — | 3 | 3 | 5 | 4 | 5 | 5 | 5 | 4 | 0 |
| 23 | 1.0 | Pre | 0 | 0 | 2 | 0 | 0 | 4 | 2 | 5 | 3 | 0 | 0 | — | 2 | 0 | 3 | — | 2 | 4 | 5 | 4 | 4 | 4 | 3 | 0 |
| | | Post | 0 | 0 | 0 | 0 | 0 | 0 | 0 | 0 | 0 | 0 | 0 | 0 | 0 | 0 | 0 | 0 | 0 | 0 | — | 0 | — | — | 2 | 0 | 0 |
| 24 | 5.0 | Pre | 0 | 1 | 0 | 1 | 0 | 4 | 5 | 0 | 3 | 3 | 0 | 0 | 0 | 0 | 0 | 3 | 5 | 4 | 5 | 5 | 4 | 4 | 4 | 2 | 0 |
| | | Post | 1 | 0 | 0 | 0 | 0 | 0 | 0 | 0 | 0 | — | — | 0 | 0 | 0 | 0 | — | 4 | 0 | 0 | 0 | 3 | 0 | — | — | 0 |
| 26 | 1.0 | Pre | 4 | 4 | — | 2 | 2 | 2 | 4 | 0 | 3 | 3 | — | — | — | 0 | 2 | 3 | 2 | 0 | 3 | 5 | 5 | 0 | 5 | 3 | 0 |
| | | Post | 2 | 2 | 0 | 0 | 4 | 5 | 0 | 2 | 0 | 3 | 0 | 0 | 0 | — | 0 | — | 4 | 4 | 5 | 5 | 4 | 3 | 0 | 4 | 0 |
| 28 | 1.0 | Pre | 3 | 1 | 1 | 2 | 3 | 4 | 2 | 0 | 3 | 4 | — | — | 0 | 0 | 3 | — | 3 | 5 | 5 | 4 | 5 | 3 | 3 | 0 | 0 |
| | | Post | 4 | 0 | 0 | 0 | 4 | 3 | 0 | 0 | 3 | 4 | — | — | 3 | — | 3 | — | 3 | 2 | 5 | 5 | 5 | 4 | 4 | 0 | 0 |
| 30 | 0.2 | Pre | 3 | 2 | 0 | 0 | 0 | 5 | 2 | 0 | 3 | 4 | — | — | 0 | 0 | 4 | — | 4 | 2 | 5 | 5 | 5 | 5 | 4 | 0 | 0 |
| | | Post | 0 | 0 | 1 | 1 | 2 | 3 | 1 | 2 | 0 | — | 5 | — | — | 0 | 2 | 3 | — | 2 | 4 | 5 | 5 | 5 | 3 | 2 | — |
| 31 | 5.0 | Pre | 5 | 2 | 0 | 0 | 0 | 5 | 1 | 0 | — | 0 | 5 | — | — | 2 | — | 3 | — | 2 | 3 | 5 | 5 | 5 | 3 | 5 | 0 |
| | | Post | 3 | 0 | 0 | 0 | 0 | 2 | 0 | 0 | 0 | — | 0 | 5 | — | 2 | — | 3 | — | 3 | 3 | 4 | 5 | 4 | 0 | 4 | 0 |
| 32 | 3.0 | Pre | 0 | 1 | 0 | 0 | 2 | 3 | 2 | 0 | 0 | 0 | — | — | 0 | 2 | — | 3 | 4 | 4 | 2 | 4 | 5 | — | 4 | 3 | 1 |
| 33 | 5.0 | Pre | 4 | 0 | 0 | 1 | 0 | 4 | 2 | 0 | 0 | 0 | — | — | 0 | 2 | 3 | — | 2 | 4 | 5 | 5 | 4 | 4 | — | 1 | 0 |
| | | Post | 0 | 1 | 2 | 4 | 4 | 3 | 0 | 0 | 0 | — | — | — | 2 | 0 | 2 | — | 3 | 3 | 4 | — | 4 | 3 | — | 2 | — |
| 34 | 0.2 | Pre | 4 | 4 | — | 0 | 3 | 5 | 4 | 0 | 3 | 4 | — | — | 3 | 2 | 2 | — | 4 | 5 | 5 | 5 | 5 | 4 | 4 | 4 | 1 |
| | | Post | 1 | 1 | 1 | 5 | — | — | 0 | 2 | — | 4 | — | — | — | — | — | — | 3 | — | 4 | 5 | 5 | — | 2 | 2 | — |
| 36 | 1.0 | Pre | 4 | 4 | 3 | 2 | 4 | 5 | 5 | 4 | 4 | 5 | — | 3 | 5 | 0 | 3 | — | 5 | 5 | 5 | 5 | 5 | 5 | 4 | 4 | 0 |
| | | Post | 3 | 1 | 0 | 0 | 4 | 3 | 2 | 3 | 4 | 5 | — | — | 3 | — | 0 | — | 4 | 3 | 4 | 5 | 4 | 3 | 4 | 2 | 0 |
| 38 | 1.0 | Pre | 4 | 4 | 3 | 2 | 4 | 5 | 2 | 2 | 3 | 5 | 5 | 5 | 5 | 2 | 5 | 3 | 5 | 5 | 5 | 5 | 5 | 5 | 5 | 5 | 1 |
| | | Post | 0 | 0 | 0 | 0 | 3 | 3 | 2 | 0 | 3 | 5 | 3 | 4 | 5 | — | 5 | — | 5 | — | 5 | 5 | 5 | 5 | 2 | 2 | — |
| 39 | 1.0 | Pre | 5 | 2 | 0 | 2 | 5 | 5 | 4 | 0 | 4 | 5 | 5 | 4 | 5 | 3 | 2 | — | 5 | 4 | 5 | 5 | 5 | 3 | 5 | 2 | 0 |
| | | Post | 3 | 0 | 0 | 3 | 1 | 3 | 2 | 0 | 3 | 2 | — | — | — | — | 2 | — | 5 | 2 | 5 | 5 | 5 | 0 | 2 | 0 | 2 |
| 40 | 1.0 | Pre | 4 | 4 | 1 | 4 | 3 | 5 | 4 | 0 | 4 | 5 | 5 | 4 | 5 | — | 5 | 3 | 5 | 5 | 5 | 5 | 5 | 4 | 5 | 5 | 2 |
| | | Post | 0 | 1 | 1 | 1 | 5 | 5 | 2 | 1 | 2 | 2 | 2 | — | 2 | 2 | 2 | — | 4 | 4 | 5 | 5 | 4 | 4 | 4 | 4 | — |
| 41 | 0.2 | Pre | 4 | 0 | 0 | 3 | 3 | 3 | 4 | 1 | — | 5 | 5 | — | 5 | 0 | 5 | 2 | 4 | 5 | 5 | 5 | 5 | 5 | 4 | 3 | 0 |
| | | Post | 0 | 0 | 1 | 2 | 2 | 3 | 0 | — | 1 | 1 | 2 | — | — | 0 | 0 | — | 3 | 3 | 3 | 3 | 3 | — | 3 | 2 | 0 |
| 42 | 1.0 | Pre | 4 | 4 | 0 | 2 | 4 | 5 | 4 | 4 | 2 | 5 | 5 | 5 | 5 | 2 | 5 | 2 | 4 | 5 | 5 | 5 | 5 | 4 | 4 | 2 | 0 |
| | | Post | 0 | 2 | 1 | 2 | 2 | 3 | 0 | — | 2 | 0 | 5 | — | — | 0 | 5 | — | 3 | 4 | 5 | 2 | 5 | 2 | 2 | 2 | — |
| 43 | 1.0 | Pre | 4 | 0 | 0 | 2 | 2 | 3 | 0 | 0 | 4 | 5 | 2 | 2 | 5 | 0 | 2 | — | 4 | 4 | 5 | 5 | 4 | 4 | 5 | 5 | 2 |
| | | Post | 1 | 3 | 1 | — | 3 | 4 | 3 | 4 | 2 | — | — | 5 | 4 | 2 | — | — | 4 | 4 | 5 | 5 | 5 | — | 2 | 1 | 0 |
| 44 | 0.2 | Pre | 4 | 1 | — | 3 | 2 | 4 | 3 | 4 | 2 | — | — | 5 | 4 | — | — | — | 4 | 5 | 5 | 5 | 4 | 4 | 2 | — | 0 |

TABLE 2-continued

| COMPOUND NO | RATE OF APPLICATION kg/ha | PRE- OR POST-EMERGENCE APPLICATION | TEST PLANTS | | | | | | | | | | | | | | | | | | | | | | | | | | |
|---|---|---|---|---|---|---|---|---|---|---|---|---|---|---|---|---|---|---|---|---|---|---|---|---|---|---|---|---|---|
| | | | Sb | Rp | Ct | Sy | Mz | Ww | Rc | Sn | Ip | Am | Pi | Ca | Po | Xs | Ab | Cv | Ot/Av | Dg | Pu | St | Ec | Sh | Ag | Cn |
| 45 | 1.0 | Post | 0 | 3 | 0 | 3 | 1 | 2 | 1 | 0 | 3 | — | 1 | 2 | — | 0 | 2 | 2 | 3 | 4 | 3 | 2 | 0 | 0 | 0 | 0 |
| 46 | 5.0 | Pre | 3 | 1 | 0 | 0 | 0 | 2 | 0 | 0 | 0 | — | 0 | 0 | 5 | 0 | 0 | — | 3 | 3 | 5 | — | 0 | 0 | 4 | 0 |
| 47 | 1.0 | Post | 0 | 0 | 0 | 0 | 0 | 0 | 0 | 0 | 0 | — | 0 | — | 0 | 0 | 0 | — | 0 | 2 | 0 | 0 | 0 | 0 | 0 | 0 |
| 48 | 5.0 | Pre | 0 | 0 | 0 | 0 | 0 | 4 | 1 | 3 | 1 | 4 | 5 | 2 | 2 | 1 | 0 | — | 4 | 4 | 3 | 2 | 2 | 3 | 1 | — |
| 51 | 0.05 | Post | 4 | 0 | 1 | 2 | 0 | 0 | 0 | 0 | 0 | — | 0 | — | 0 | — | 0 | — | 3 | 3 | 0 | 2 | 0 | 0 | 0 | 0 |
| 51 | 0.2 | Pre | 0 | 0 | 0 | 2 | 2 | 5 | 0 | 0 | 0 | 3 | — | 2 | 5 | 0 | 2 | — | 3 | 5 | 5 | 5 | 2 | — | 5 | 0 |
| 52 | 0.2 | Post | 0 | 0 | 0 | 0 | 1 | 2 | 3 | 5 | 5 | 5 | 1 | 4 | 0 | 0 | 4 | — | 3 | 2 | 1 | 5 | 1 | 1 | 1 | 5 |
| 53 | 5.0 | Pre | 3 | 1 | 0 | 3 | — | 3 | 0 | 3 | 3 | — | — | — | 5 | 0 | — | 2 | 2 | 4 | — | — | 5 | 2 | 5 | — | — |
| 54 | 5.0 | Pre | 1 | 0 | 0 | 0 | 2 | 3 | 0 | 2 | 0 | 4 | 5 | 2 | 2 | 0 | 5 | 3 | 5 | 4 | 5 | 4 | 4 | 1 | 4 | 3 | — |
| 55 | 5.0 | Pre | 2 | 1 | 0 | 0 | — | 5 | 2 | — | 2 | 4 | 2 | 3 | 2 | 0 | 2 | — | 4 | 4 | 4 | 4 | 0 | 0 | 0 | 0 | 0 |
| 56 | 5.0 | Post | 0 | 0 | 0 | 0 | 0 | 4 | 1 | — | 4 | 4 | 5 | — | — | 0 | 4 | 3 | 5 | 4 | 4 | 4 | 0 | — | 5 | 5 | — |
| 59 | 4.0 | Pre | 0 | 0 | 0 | — | 0 | 0 | — | 0 | 0 | — | — | 2 | 2 | — | 0 | — | — | 0 | — | — | 5 | 5 | — | 5 | 5 |
| 61 | 1.0 | Pre | 0 | 0 | 0 | 2 | 0 | 0 | 0 | 0 | 0 | 5 | 0 | 0 | 0 | 0 | 0 | — | 0 | 0 | — | 0 | 0 | 0 | 0 | 0 | 0 |
| 62 | 0.05 | Post | 0 | 0 | 0 | 0 | 2 | 0 | 0 | 3 | 3 | — | 5 | — | 5 | — | 2 | — | 4 | 5 | 5 | 5 | 5 | 3 | 3 | 5 | 3 | 0 |
| 62 | 0.2 | Pre | 0 | 0 | 0 | 0 | 2 | 3 | 0 | 0 | 0 | 3 | 0 | 3 | 3 | 0 | 0 | — | 2 | 4 | 5 | 3 | 4 | 0 | 0 | 0 | 0 |
| 63 | 1.0 | Post | 2 | 3 | 0 | 0 | 0 | 5 | 0 | 0 | 3 | — | 0 | 0 | 5 | 0 | 0 | — | 3 | 4 | 5 | 4 | 2 | 2 | 4 | 0 | 0 |
| 64 | 1.0 | Pre | 3 | 1 | 0 | 2 | 2 | 5 | 3 | 0 | 3 | — | 2 | 0 | 3 | 0 | 2 | — | 5 | 4 | 5 | 3 | 5 | 5 | 5 | 5 | 5 | — |
| 65 | 1.0 | Post | 1 | 0 | 2 | 3 | 2 | 3 | 2 | 2 | 2 | 5 | 0 | 2 | 5 | 0 | 2 | — | 4 | 2 | 4 | 4 | 3 | 3 | 3 | 3 | 1 | — |
| 66 | 0.05 | Pre | 2 | 0 | 2 | 2 | 2 | 2 | 4 | 0 | 0 | 2 | 0 | 0 | — | 0 | — | — | 3 | 2 | — | 2 | 4 | 2 | 2 | 2 | 2 | — |
| 66 | 0.2 | Post | 4 | 4 | 2 | 4 | 5 | 5 | 4 | 4 | 4 | 5 | 5 | 3 | — | 0 | 4 | — | 5 | 3 | — | 4 | 5 | 2 | — | 1 | 0 | — |
| 69 | 1.0 | Pre | 2 | 1 | 1 | 3 | 3 | 3 | 1 | 2 | 1 | 3 | — | — | 2 | 0 | 2 | — | 4 | 3 | — | 1 | 3 | 2 | 3 | 2 | 2 | — |
| 70 | 1.0 | Post | 0 | 0 | 0 | 0 | 0 | — | 0 | 0 | 0 | — | 1 | — | — | 0 | 0 | — | 0 | 0 | — | 1 | — | 0 | — | 1 | — | — |
| 71 | 1.0 | Pre | 1 | 0 | 0 | 0 | 2 | 4 | 1 | 0 | 0 | — | — | — | — | 0 | 2 | — | 3 | 2 | — | 4 | 2 | 0 | 2 | 0 | — | — |
| 72 | 5.0 | Post | 0 | 0 | 0 | 0 | 2 | 1 | 0 | 0 | 0 | 5 | 4 | 5 | — | 0 | 0 | — | 0 | 3 | — | 5 | 4 | 2 | 3 | 2 | 4 | — |
| 73 | 5.0 | Pre | 0 | 0 | 0 | 0 | 2 | 5 | 2 | 3 | 0 | 3 | 2 | 0 | 0 | 0 | 0 | — | 4 | 3 | — | 0 | — | — | — | — | — | — |
| 74 | 1.0 | Post | 0 | 0 | 0 | 0 | — | 0 | 0 | 0 | 0 | — | 0 | 0 | 0 | 0 | 0 | — | 4 | 0 | — | 0 | 0 | 2 | 0 | 2 | 0 | — |
| 75 | 5.0 | Pre | 0 | 0 | 0 | 1 | 1 | 4 | 0 | 0 | 0 | 0 | 0 | 2 | — | 0 | 0 | — | 0 | 0 | — | 1 | 1 | 0 | 0 | 0 | 0 | — |
| 78 | 5.0 | Pre | 0 | 0 | 0 | 1 | 0 | 4 | 0 | 2 | 0 | 5 | — | 4 | 4 | 0 | 0 | — | 4 | 0 | — | 3 | — | 0 | 2 | 4 | 4 | — |

TABLE 2-continued

| COMPOUND NO | RATE OF APPLICATION kg/ha | PRE- OR POST-EMERGENCE APPLICATION | Sb | Rp | Ct | Sy | Mz | Ww | Rc | Sn | Ip | Am | Pi | Ca | Po | Xs | Ab | Cv | Ot/Av | Dg | Pu | St | Ec | Sh | Ag | Cn |
|---|---|---|---|---|---|---|---|---|---|---|---|---|---|---|---|---|---|---|---|---|---|---|---|---|---|---|
| 81 | 1.0 | Post | 0 | 0 | 0 | 0 | 0 | 0 | 0 | 0 | 0 | 0 | 0 | 0 | — | — | 0 | — | 1 | 0 | — | 0 | 0 | 0 | 0 | 0 | 0 |
|  |  | Pre | 4 | 3 | 2 | 4 | 3 | 1 | 3 | 4 | 3 | 0 | — | 4 | — | 0 | 4 | — | 5 | 4 | — | 5 | 5 | 3 | 1 | 0 | 0 |
| 82 | 5.0 | Post | 2 | 1 | 0 | 2 | 3 | 4 | 1 | 1 | 3 | — | — | 2 | — | 0 | — | — | 3 | 3 | — | 5 | 3 | 3 | 2 | 0 | 0 |
|  |  | Pre | 0 | — | 0 | 0 | 0 | 5 | 0 | 0 | 1 | 0 | — | 0 | — | 0 | 0 | — | 3 | 1 | — | 0 | 0 | 0 | 0 | 0 | — |
| 83 | 1.0 | Post | 0 | 0 | 0 | 1 | 2 | 3 | 3 | 0 | 0 | 0 | 0 | 4 | — | 0 | 0 | — | 1 | 0 | — | 0 | 0 | 0 | 1 | 0 | 0 |
|  |  | Pre | 3 | 0 | 0 | 2 | 2 | 2 | 0 | 0 | 0 | — | 0 | 0 | — | 0 | 2 | — | 1 | 4 | — | 1 | 3 | 0 | 0 | 0 | 0 |
| 84 | 1.0 | Post | 0 | 0 | 0 | 0 | 1 | 0 | 2 | 0 | 0 | — | — | 4 | — | 0 | — | — | 1 | 4 | — | 3 | 2 | 1 | 0 | 0 | 0 |
|  |  | Pre | 0 | 0 | 1 | 2 | 2 | 2 | 2 | 0 | 3 | — | 0 | 2 | — | 0 | 2 | — | 1 | 0 | — | 0 | — | — | 0 | 0 | — |
| 85 | 4.0 | Post | 0 | 0 | 2 | 1 | 1 | 4 | 3 | 0 | 0 | 2 | — | 2 | — | 0 | — | — | 3 | 2 | — | 3 | 1 | 1 | 0 | — | — |
|  |  | Pre | 2 | — | 1 | 1 | 2 | 2 | 0 | 1 | 0 | 0 | 4 | 0 | — | 0 | 1 | — | 2 | 3 | — | 2 | 4 | 2 | 0 | 0 | 0 |
| 91 | 1.0 | Post | 0 | 1 | 1 | 3 | 1 | 2 | 2 | 3 | 0 | 2 | — | 5 | — | 1 | — | — | 2 | 5 | — | 2 | 3 | 0 | 0 | — | — |
|  |  | Pre | 5 | 4 | 4 | 1 | 5 | 4 | 4 | 2 | 3 | 2 | 0 | 5 | — | 2 | 5 | — | 5 | 5 | — | 5 | 5 | 4 | 5 | — | — |
| 92 | 1.0 | Post | 3 | 2 | 1 | — | 3 | 2 | 0 | 5 | 0 | 2 | — | 5 | — | 2 | 2 | — | 2 | 3 | — | 1 | 1 | 2 | 1 | — | — |
|  |  | Pre | — | 3 | 1 | 3 | 1 | 3 | 4 | 0 | 3 | 0 | — | 0 | — | 0 | 5 | — | 3 | 5 | — | 5 | 5 | 0 | — | — | — |
| 95 | 0.2 | Post | — | 1 | — | — | — | 1 | 0 | 3 | — | 1 | — | — | — | 0 | — | — | 3 | 4 | — | 3 | 4 | 3 | — | — | — |
|  |  | Pre | 5 | 2 | 0 | 2 | 2 | 5 | 3 | — | — | 5 | 0 | 5 | — | 0 | 2 | — | 4 | 5 | — | 5 | 4 | 1 | — | — | — |
| 96 | 1.0 | Post | — | 0 | 1 | — | 2 | 4 | 0 | — | 0 | 3 | — | 0 | — | 0 | 4 | — | 1 | 3 | — | 4 | 0 | 0 | 2 | — | — |
|  |  | Pre | 4 | 4 | 4 | 1 | 4 | 5 | 3 | 5 | — | 3 | — | 5 | — | 1 | — | — | 5 | 5 | — | 5 | 3 | 4 | — | — | — |
| 97 | 1.0 | Post | — | 1 | — | 2 | 3 | 4 | — | 0 | — | 3 | — | 0 | — | 0 | 2 | — | 2 | 3 | — | 3 | 3 | 3 | 2 | — | — |
|  |  | Pre | 4 | 4 | 4 | 4 | 5 | 5 | 5 | 5 | 4 | 5 | 5 | 5 | — | 4 | 5 | — | 4 | 4 | — | 4 | 4 | 4 | 4 | — | — |
| 98 | 1.0 | Post | 4 | 3 | 0 | 3 | 4 | 4 | 5 | 4 | 3 | 3 | 5 | 2 | — | 3 | 3 | — | 5 | 4 | — | 5 | 5 | 4 | 4 | — | — |
|  |  | Pre | 2 | 2 | 3 | 4 | 5 | 5 | 2 | 3 | 3 | 3 | 5 | — | — | 2 | 3 | — | 4 | 5 | — | 3 | 3 | 3 | 2 | — | — |
| 103 | 5.0 | Post | 4 | 3 | 0 | 3 | 2 | 4 | 2 | 3 | 3 | — | 2 | 3 | — | 2 | 4 | — | 4 | 4 | — | 5 | 4 | 3 | 4 | — | — |
|  |  | Pre | 1 | 4 | 3 | 3 | 3 | 4 | 0 | 3 | 3 | 0 | 3 | 3 | — | 2 | 2 | — | 5 | 3 | — | 5 | 4 | 3 | 2 | — | — |
| 104 | 1.0 | Post | 0 | 0 | 0 | 0 | 0 | 0 | 0 | 0 | 0 | 0 | 0 | 0 | — | 0 | 0 | — | 0 | 0 | — | 0 | 0 | 0 | 0 | — | — |
|  |  | Pre | 0 | 0 | 1 | 2 | 0 | 3 | 0 | 0 | 1 | 3 | 0 | 1 | — | 0 | 1 | — | 2 | 0 | — | 1 | 1 | 1 | 0 | 0 | — |
| 106 | 5.0 | Post | 0 | 0 | 0 | 0 | 2 | 0 | 0 | 0 | 0 | 0 | 0 | 0 | — | 0 | — | — | 1 | 0 | — | 0 | 0 | 0 | 0 | — | — |
|  |  | Pre | 5 | 5 | 5 | 5 | 3 | 5 | 4 | 4 | 5 | 3 | 0 | 5 | — | 4 | 5 | — | 4 | 5 | — | 5 | 5 | 5 | 5 | 4 | — |
| 109 | 1.0 | Post | 2 | 3 | 1 | 3 | 3 | 3 | 1 | 3 | 3 | 2 | 2 | 3 | — | 3 | 3 | — | 4 | 4 | — | 2 | 2 | 0 | 2 | — | — |

TABLE 3

| COMPOUND NO | RATE OF APPLICATION kg/ha | PRE- OR POST-EMERGENCE APPLICATION | TEST PLANTS ||||||||||||||||||||||||
|---|---|---|---|---|---|---|---|---|---|---|---|---|---|---|---|---|---|---|---|---|---|---|---|---|---|
| | | | Sb | Rp | Ct | Sy | Mz | Ww | Rc | Sn | Ip | Am | Pi | Ca | Ga | Xa | Ab | Co | Av | Dg | Al | St | Ec | Sh | Ag | Cn |
| 110 | 1.0 | Pre | 4 | 4 | 2 | 4 | 3 | 5 | 2 | — | 1 | 5 | — | 5 | — | 0 | 4 | 3 | 4 | 5 | 5 | 5 | 5 | 3 | 3 | — |
| | | Post | 1 | 1 | 1 | 1 | 1 | 4 | 0 | 1 | 3 | 2 | — | 1 | 2 | 1 | 2 | 0 | 4 | 3 | 3 | 3 | 1 | 2 | 1 | 5 | — |
| 111 | 1.0 | Pre | 5 | 4 | 2 | 2 | 3 | 4 | 4 | — | 2 | 5 | — | 5 | 3 | 0 | 4 | 1 | 3 | 5 | 5 | 5 | 5 | 5 | 4 | 5 | — |
| | | Post | 1 | 1 | 1 | 4 | 1 | 4 | 0 | 3 | 3 | 4 | — | 5 | 3 | 0 | 2 | 1 | 0 | 3 | 3 | 4 | 3 | 5 | 3 | 5 | — |
| 112 | 5.0 | Pre | 3 | 2 | 1 | 0 | 0 | 3 | 0 | 0 | 2 | 4 | — | 5 | — | 0 | 4 | 2 | 1 | 4 | 3 | 4 | 3 | 5 | 4 | 2 | — |
| | | Post | 0 | 0 | 0 | 0 | 2 | 0 | 0 | 2 | 3 | 0 | — | 1 | — | 1 | 0 | 0 | 0 | 0 | — | 1 | 3 | 2 | 0 | — | — |
| 117 | 1.0 | Pre | 0 | 1 | 0 | 2 | 1 | 2 | 0 | 0 | 0 | 1 | — | 0 | — | 0 | 0 | 0 | 0 | 0 | — | 0 | 0 | 3 | 0 | 0 | — |
| | | Post | 2 | 0 | 0 | 2 | 0 | 2 | 2 | 2 | 0 | 3 | — | 5 | 2 | — | 1 | 3 | 3 | 0 | 4 | 0 | 5 | 3 | 0 | 2 | — |
| 119 | 1.0 | Pre | 2 | 0 | 0 | 0 | 0 | 1 | 0 | 1 | 0 | 2 | — | 5 | — | 1 | 0 | 2 | 1 | 3 | 4 | 5 | 3 | 3 | 2 | 1 | — |
| | | Post | 2 | 0 | 0 | 1 | 1 | 3 | 2 | 1 | 2 | 3 | — | 2 | — | — | 2 | 1 | 0 | 3 | 0 | 5 | 0 | 0 | 2 | — | 2 |
| 120 | 1.0 | Pre | 4 | 3 | 0 | 2 | 3 | 4 | 2 | 0 | 3 | 4 | — | 4 | 2 | — | 0 | 4 | 2 | 2 | 4 | 5 | 5 | 3 | 2 | 5 | 0 |
| | | Post | 0 | 0 | 0 | 0 | 0 | 3 | 0 | 4 | 3 | 3 | — | 2 | 2 | — | 0 | 0 | 0 | 0 | 0 | 0 | 0 | 2 | 0 | — | — |
| 122 | 5.0 | Pre | 1 | 0 | 1 | 2 | 1 | 4 | 0 | 1 | 3 | 4 | — | 4 | 2 | — | 4 | 2 | 0 | 2 | 4 | 5 | 5 | 2 | 1 | 0 | 1 |
| | | Post | 0 | 0 | 0 | 0 | 0 | 3 | 0 | 0 | — | 3 | — | 2 | 2 | 2 | 2 | 0 | 0 | 0 | 0 | 5 | 0 | 0 | 0 | 3 | 4 |
| 125 | 0.2 | Pre | 4 | 1 | 1 | 0 | 2 | 4 | 2 | 2 | — | 0 | — | 0 | 0 | — | 0 | 4 | 1 | 2 | 4 | 5 | 4 | 4 | 0 | 0 | 0 |
| 125 | 1.0 | Post | 5 | 4 | 3 | 2 | 4 | 4 | 5 | 1 | 3 | 3 | — | 3 | 5 | 5 | — | 2 | 5 | 5 | 5 | 5 | 5 | 5 | 5 | 3 | 4 |
| 126 | 1.0 | Pre | 2 | 2 | 1 | 3 | 3 | 5 | 2 | 5 | 3 | 5 | — | 5 | 5 | 4 | — | 2 | — | 3 | 5 | 5 | 2 | 3 | — | 5 | 0 |
| | | Post | 4 | 4 | 2 | 1 | 0 | 4 | 0 | 2 | 2 | 4 | 0 | 5 | 3 | 2 | 4 | 2 | 5 | 2 | 5 | 5 | 2 | 5 | 3 | 2 | 0 |
| 127 | 5.0 | Pre | 1 | 2 | 1 | 4 | 0 | 4 | 0 | 0 | 4 | 3 | 0 | 0 | 3 | 4 | 2 | 2 | 0 | 3 | 5 | 2 | 1 | 0 | 0 | 2 | 4 |
| | | Post | 0 | 0 | 0 | 0 | 2 | 0 | 0 | 0 | 2 | 0 | — | 0 | — | 0 | 0 | 3 | — | 2 | 3 | 2 | 1 | 0 | 5 | 2 | 0 | 0 |
| 134 | .025 | Pre | — | — | 0 | 0 | — | 0 | 0 | — | — | — | 0 | — | 0 | — | — | — | — | — | — | — | — | — | 0 | 0 | 0 |
| 134 | 1.0 | Post | 1 | 3 | 0 | 0 | — | 5 | 3 | 3 | 4 | 4 | — | 4 | 3 | 3 | — | 5 | 3 | 5 | 5 | 3 | 5 | 5 | 4 | 5 | 2 |
| 136 | 1.0 | Pre | 5 | 5 | 0 | 2 | — | 4 | 0 | 2 | 2 | 3 | — | 3 | — | 2 | — | 2 | — | 3 | 3 | — | 2 | — | 1 | — | — | — |
| 138 | 5.0 | Post | 3 | 3 | 0 | 3 | 2 | 4 | 5 | 0 | 2 | 2 | 3 | 0 | — | — | — | 3 | 2 | 4 | 5 | 4 | 4 | 0 | 4 | — | — | — |
| 141 | 1.0 | Pre | — | — | — | — | — | 2 | — | — | — | — | — | — | — | — | — | — | — | — | — | — | — | — | — | — | — |
| | | Post | 4 | 2 | 1 | 4 | 2 | 4 | 3 | 3 | 4 | 3 | — | 4 | — | 3 | — | 5 | 3 | 5 | 5 | 3 | 5 | 5 | 4 | 5 | 2 |
| 144 | 1.0 | Pre | 2 | 2 | 0 | 2 | 2 | 2 | 0 | 2 | 2 | 2 | — | 3 | — | — | — | 2 | 2 | 3 | 3 | 5 | 2 | 2 | 5 | — | — | — |
| | | Post | 1 | 1 | 0 | 0 | 1 | 2 | 2 | 0 | 2 | 3 | — | 3 | — | — | — | 5 | — | 5 | 5 | 5 | 5 | 2 | 5 | 5 | 2 | 1 |
| 146 | 1.0 | Pre | 3 | 2 | 0 | 1 | 2 | 3 | 2 | 0 | 2 | 2 | 0 | 0 | — | — | — | 2 | 1 | 4 | — | 3 | 0 | 2 | 0 | 0 | 0 | 3 |
| | | Post | 0 | 0 | 1 | 0 | 0 | 2 | 2 | 0 | 1 | 3 | 0 | 0 | — | — | — | 0 | 0 | 2 | 4 | — | — | 2 | 2 | 0 | 3 | — |
| 148 | 1.0 | Pre | 0 | 0 | 0 | — | — | 2 | 0 | — | 2 | 1 | 1 | 0 | — | — | — | 2 | — | 2 | 0 | 0 | 1 | — | 1 | 0 | 0 | 0 |
| | | Post | 0 | 0 | 0 | 1 | 1 | 2 | 0 | 0 | 2 | 2 | 2 | 3 | — | 2 | — | 1 | 0 | 3 | 3 | 2 | 2 | 0 | 3 | 0 | 3 | 0 |
| 153 | 1.0 | Pre | 2 | 0 | 0 | 1 | 2 | 3 | 1 | 0 | 2 | 0 | 0 | 2 | 0 | 0 | 0 | 2 | 0 | 3 | 3 | 2 | 2 | 2 | 0 | 3 | 0 |
| | | Post | 0 | 0 | 1 | 0 | 2 | 2 | 0 | 1 | 2 | 0 | — | 2 | 0 | 0 | 0 | 1 | 0 | 2 | 2 | 0 | 3 | 0 | 0 | 0 | 2 | 0 |

Names of test plants in Tables 2 and 3
Sb: Sugar beet
Rp: Rape
Ct: Cotton
Sy: Soya Bean
Mz: Maize
Ww: Winter wheat
Rc: Rice
Sn: *Senecio vulgaris*
Ip: *Ipomoea purpurea*
Am: *Amaranthus retroflexus*
Pi: *Polygonum aviculare*
Ca: *Chenopodium album*
Po: *Portulaca oleracea* the test compound, whereas in the previous test the seeds were sprayed directly.

The compounds were formulated in a similar way to that described in Example 10, but using cyclohexanone solution containing Synperonic NPE 1800 (a nonylphenolpropylene oxide-ethylene oxide condensate) and Tween 85 (a condensate of sorbitan tri-oleate with 20 molar proportions of ethylene oxide) instead of the methylcyclohexanone solution of surfactants described in that Example. The damage to the test plants was assessed on a scale of 0 to 9 where 0 represents 0 to 10% damage to the plant and 9 is 90 to 100% damage. Assessments were made 26 days after spraying the compounds. The results are given in Tables 4 and 5 below.

TABLE 4

| COMPOUND NO | RATE OF APPLICATION kg/ha | PRE- OR POST-EMERGENCE APPLICATION | TEST PLANTS | | | | | | | | | | | | | | | |
|---|---|---|---|---|---|---|---|---|---|---|---|---|---|---|---|---|---|---|
| | | | Ww | Br | Pe | Rp | Sb | Lt | Av | Al | Bt | Ag | Ga | Sm | Ca | Pi | Ma | Sp |
| 18 | 0.2 | Pre | 6 | 7 | 2 | 8 | 9 | 7 | 9 | 9 | 9 | 6 | 7 | 9 | 9 | 9 | 9 | 6 |
| | | Post | 8 | 7 | 1 | 0 | 1 | 0 | 8 | 3 | 0 | 5 | 7 | 7 | 4 | 7 | 0 | — |
| 20 | 0.1 | Pre | 8 | 9 | 0 | 0 | 9 | 0 | 9 | 9 | 9 | 9 | 5 | 9 | 9 | 9 | 8 | 3 |
| | 0.2 | Pre | 9 | 9 | 2 | 7 | 6 | 5 | 9 | 9 | 9 | 9 | 9 | 9 | 9 | 9 | 8 | 4 |
| | 0.1 | Post | 8 | 6 | 0 | 0 | 1 | 0 | 3 | 1 | 0 | 1 | 5 | 3 | 3 | 4 | 1 | 4 |
| | 0.2 | Post | 9 | 8 | 0 | 0 | 1 | 0 | 5 | 5 | 2 | 5 | 7 | 5 | 2 | 9 | 2 | 6 |
| | 0.4 | Post | 9 | 9 | 3 | 0 | 3 | 0 | 9 | 6 | 7 | 9 | 7 | 7 | 6 | 9 | 3 | 6 |
| 22 | 0.1 | Pre | 7 | 8 | 0 | 0 | 5 | 1 | 9 | 9 | 9 | 8 | 8 | 8 | 9 | 9 | 7 | 1 |
| | 0.2 | Pre | 9 | 9 | 0 | 3 | 8 | 2 | 9 | 9 | 9 | 9 | 9 | 9 | 9 | 9 | 6 | 3 |
| | 0.1 | Post | 7 | 7 | 0 | 0 | 0 | 0 | 4 | 2 | 2 | 3 | 3 | 1 | 2 | 6 | 0 | 3 |
| | 0.2 | Post | 9 | 6 | 1 | 0 | 1 | 0 | 5 | 4 | 2 | 5 | 6 | 5 | 4 | 7 | 1 | 3 |
| | 0.4 | Post | 9 | 7 | 1 | 1 | 1 | 0 | 8 | 8 | 6 | 8 | 7 | 6 | 6 | 7 | 1 | 3 |

Xs and Xa: *Xanthium spinosum*
Ab: *Abutilon theophrastii*
Cv: *Convolvulus arvensis*
Ot/Av: Oats (cultivated in pre-emergence test and *Avena fatua* (wild oats) in post-emergence test) (Applies to Table 2; in Table 3 only *Avena fatua* is used)
Dg: *Digitaria sanguinalis*
Pu: *Poa annua*
St: *Setaria viridis*
Ec: *Echinochloa crus-galli*
Sh: *Sorghum halepense*
Ag: *Agropyron repens*
Cn: *Cyperus rotundus*
Ga: *Galium aparine*
Co: *Cassia obtusifolia*
Al: *Alopecurus myosuroides*

The names of the test plants in Table 4

Ww: Winter wheat
Br: Barley
Pe: Peas
Rp: Rape
Sb: Sugar beet
Lt: Lettuce
Av: *Avena fatua*
Al: *Alopecurus myosuroides*
Bt: *Bromus tectorum*
Ag: *Agropyron repens*
Ga: *Galium aparine*
Sm: *Stellaria media*
Ca: *Chenopodium album*
Pi: *Polygonum aviculare*
Ma: *Matricaria inodora*
Sp: *Sinapis alba*

TABLE 5

| COMPOUND NO | RATE OF APPLICATION kg/ha | TEST PLANTS | | | | | | | | | | | | | | | | | | |
|---|---|---|---|---|---|---|---|---|---|---|---|---|---|---|---|---|---|---|---|---|
| | | Mz | Rc | Sy | Ct | To | Sg | Eh | Ip | Ab | Se | Si | Ds | Xa | Ec | Dg | St | Sh | Pm | Cd | Cn |
| 2 | 1.1 | 9 | 7 | 2 | 2 | 5 | 5 | 4 | 1 | 2 | 1 | 2 | 4 | 0 | 1 | 8 | 6 | 2 | — | 0 | 0 |
| 4 | 1.1 | 7 | 8 | 3 | 2 | 5 | 8 | 4 | 6 | 6 | 7 | 7 | 6 | 2 | 3 | 9 | 9 | 4 | — | 4 | 0 |
| 18 | 0.4 | 0 | 1 | 2 | 1 | 1 | 3 | 2 | 3 | 1 | 2 | 2 | 3 | 0 | 0 | 1 | 5 | 1 | 7 | 1 | 0 |
| 20 | 0.2 | 7 | 4 | 2 | 1 | 1 | 4 | 4 | 5 | 2 | 2 | 1 | 5 | 1 | 0 | 8 | 6 | 0 | 5 | 0 | 0 |
| 22 | 0.4 | 7 | 7 | 2 | 2 | 1 | 3 | 5 | 6 | 1 | 4 | 4 | 4 | 0 | 3 | 7 | 7 | 4 | 7 | 0 | 0 |

EXAMPLE 11

This Example further illustrates the herbicidal properties of compounds according to the invention. Tests were carried out as described in Example 10, but using different ranges of test plants. The post-emergence test was slightly different from the one described in Example 10 in that the seeds were sown in trays of soil and covered with a few millimeters of soil before spraying The names of test plants in Table 5

Mz: Maise
Rc: Rice
Sy: Soya bean
Ct: Cotton
To: Tomato
Sg: Sorghum
Eh: *Euphorbia heterophylla*

Ip: *Ipomoea purpurea*
Ab: *Abutilon theophrasti*
Se: *Sesbania exaltata*
Si: *Sida spinosa*
Ds: *Datura stramonium*
Xa: *Xanthium pensylvanicum*
Ec: *Echinochloa crus-galli*
Dg: *Digitaria sanguinalis*
St: *Setaria viridis*
Sh: *Sorghum halepense*
Pm: *Panicum maximum*
Cd: *Cyperus difformis*
Cn: *Cyperus rotundus*

EXAMPLE 12

This Example illustrates a composition according to the invention which comprises an emulsifiable concentrate. The following ingredients were thoroughly mixed to give a solution.

| | |
|---|---|
| Compound No. 2 of Table I | 10% |
| Ethylene dichloride | 40% |
| Calcium dodecylbenzenesulphate | 5% |
| "Lubrol" L | 10% |
| "Aromasol" H | 35% |

EXAMPLE 13

A composition in the form of grains readily dispersible in a liquid, e.g. water, was prepared by grinding together the first three ingredients in the presence of added water and then mixing in the sodium acetate. The resultant mixture was dried and passed through a British Standard mesh sieve, size 44–100, to obtain the desired size of grains.

| | |
|---|---|
| Compound No. 4 of Table I | 50% |
| "Dispersol" T | 25% |
| "Lubrol" APN 5 | 1.5% |
| Sodium acetate | 23.5% |

EXAMPLE 14

The following ingredients were ground together to produce a powder formulation readily dispersible in liquids.

| | |
|---|---|
| Compound No. 8 of Table I | 45% |
| "Dispersol" T | 5% |
| "Lissapol" NX | 0.5% |
| "Cellofas" B600 | 2% |
| Sodium acetate | 47.5% |

EXAMPLE 15

The active ingredient was dissolved in acetone and the resultant liquid was sprayed on to the granules of china clay. The solvent was then allowed to evaporate to produce a granular composition.

| | |
|---|---|
| Compound No. 18 of Table I | 5% |
| China clay granules | 95% |

EXAMPLE 16

A composition suitable for use as a seed dressing was prepared by mixing the following three ingredients.

| | |
|---|---|
| Compound No. 2 of Table I | 50% |
| Mineral oil | 2% |
| China clay | 48% |

EXAMPLE 17

A dusting powder was prepared by mixing the active ingredient with talc.

| | |
|---|---|
| Compound No. 4 of Table I | 5% |
| Talc | 95% |

EXAMPLE 18

A Col formulation was prepared by ball-milling the constituents set out below and then forming an aqueous suspension of the ground mixture with water.

| | |
|---|---|
| Compound No. 8 of Table I | 40% |
| "Dispersol" T | 10% |
| "Lubrol" APN5 | 1% |
| Water | 49% |

EXAMPLE 19

A dispersible powder formulation was made by mixing together the ingredients set out below and then grinding the mixture until all were thoroughly mixed.

| | |
|---|---|
| Compound No. 18 of Table I | 25% |
| "Aerosol" OT/B | 2% |
| "Dispersol" A.C. | 5% |
| China clay | 28% |
| Silica | 40% |

EXAMPLE 20

This Example illustrates the preparation of a dispersible powder formulation. The ingredients were mixed and the mixture then ground in a comminution mill.

| | |
|---|---|
| Compound No. 20 of Table I | 25% |
| "PERMINAL" BX | 1% |
| "Dispersol" T | 5% |
| Polyvinylpyrrolidone | 10% |
| Silica | 25% |
| China clay | 34% |

EXAMPLE 21

The ingredients set out below were formulated into a dispersible powder by mixing then grinding the ingredients.

| | |
|---|---|
| Compound No. 2 of Table I | 25% |
| "Aerosol" OT/B | 2% |
| "Dispersol" A | 5% |
| China clay | 68% |

In Examples 1 to 10 the proportions of the ingredients given are by weight and the Examples were all repeated using, as active ingredient, the other compounds of Table I.

There now follows an explanation of the compositions or substances represented by the various Trade Marks and Trade Names mentioned above.

LUBROL L: a condensate of nonyl phenol (1 mole) with ethylene oxide (13 moles).

AROMASOL H: a solvent mixture of alkylbenzenes

DISPERSOL T AND AC: a mixture of sodium sulphate and a condensate of formaldehyde with sodium naphthalene sulphonate LUBROL APN 5: a condensate of nonyl phenol (1 mole) with ethylene oxide (5.5 moles)

CELLOFAS B600: a sodium carboxymethyl cellulose thickener.

EXAMPLE 22

The compounds were tested against a variety of foliar fungal diseases of plants. The techniques employed were as follows:

The plants were grown in John Innes Potting Compost (No. 1 or 2) in 4 cm diameter mini-pots. A layer of fine sand was placed at the bottom to facilitate uptake of test compound by the roots. The test compounds were formulated either by bead milling with aqueous Dispersol T or as a solution in acetone or acetone/ethanol which was diluted to the required concentration immediately before use. For the foliage diseases suspensions (100 ppm active ingredient) were sprayed on to the foliage and applied to the roots of the same plant via the soil. Exceptions were the tests on *Plasmopara viticola* and *Venturia inaequalis* in which the compound was sprayed on to the foliage only. Sprays were applied to maximum retention, and root drenches were applied to a final concentration equivalent to approximately 40 ppm a.i./dry soil. Tween 20, to give a final concentration of 0.05% was added when the sprays were applied to cereals.

For most of the tests the compound was applied to the soil (roots) and to the foliage (by spraying) one or two days before the plant was inoculated with the diseases. An exception was the test on *Erysiphe graminis* in which the plants were inoculated 24 hours before treatment. After inoculation, the plants were put into an appropriate environment to allow infection to take place and then incubated until the disease was ready for assessment.

The period between inoculation and assessment varied from four to fourteen days according to the disease and environment.

The disease control was recorded by the following grading:

4 = no disease
3 = trace-5% of disease on untreated plants
2 = 6-25% of disease on untreated plants
1 = 26-59% of disease on untreated plants
0 = 60-100% of disease on untreated plants The results are shown in Table 6 below.

In the table below the following compounds have been omitted for the reasons stated.

Compounds Nos. 5, 6, 7, 14, 16, 21, 23, 25, 27, 29, 32, 40, 58, 88, 115, 123, 140 were not tested at the standard primary screen rate.

Compounds Nos. 135, 136, 138, 142-145, 147, 148 and 160 were not tested.

A dash, thus "—", in the table in any column indicates that the particular compound was not tested against that particular disease.

An asterisk, thus "*" against the disease grading in the column headed "*BOTRYTIS CINEREA* (TOMATO)" signifies that the test plant material used in this instance were grape berries.

TABLE 6

| COMPOUND NUMBER | PUCCINIA BECONDITA (WHEAT) | ERYSIPHE GRAMINIS (BARLEY) | PLASMOPARA VITICOLA (VINE) | PHYTOPHTHORA INFESTANS (TOMATO) | BOTRYTIS CINEREA (TOMATO) | CERCOSPORA ARACHIDICOLA (PEANUT) | VENTURIA INEQUALIS (APPLE) |
|---|---|---|---|---|---|---|---|
| 1 | 0 | 0 | 0 | 2 | 0 | 0 | 2 |
| 2 | 0 | 4 | 3 | 3 | 0 | 3 | 3 |
| 3 | 0 | 0 | 0 | 0 | 0 | 0 | 1 |
| 4 | 0 | 0 | 4 | 4 | 0 | 3 | 0 |
| 8 | 0 | 1 | 4 | 4 | 0 | 3 | — |
| 9 | 0 | 0 | 0 | 0 | 0 | 1 | 0 |
| 10 | 0 | 0 | 0 | 0 | 0 | 1 | 0 |
| 11 | 0 | 1 | 0 | 0 | 2 | 0 | 1 |
| 12 | 0 | 0 | 0 | 0 | 0 | 0 | 0 |
| 13 | 0 | 0 | 0 | 0 | 0 | 3 | 0 |
| 15 | 0 | 0 | 0 | 1 | 0 | 2 | 0 |
| 17 | 0 | 0 | 0 | 2 | 0 | 2 | 0 |
| 18 | 0 | 0 | 4 | 4 | 0 | 4 | 0 |
| 19 | 0 | 0 | 2 | 1 | 0 | 0 | 0 |
| 20 | — | 4 | 4 | 3 | 1 | 3 | 0 |
| 22 | 0 | 4 | 4 | 4 | 0 | 4 | 4 |
| 24 | 0 | 0 | 4 | 3 | 0 | 0 | — |
| 26 | — | — | — | — | — | — | — |
| 29 | 0 | 0 | 4 | 3 | 0 | 1 | 0 |
| 30 | 0 | 1 | 4 | 3 | 0 | 3 |  |
| 31 | 0 | 3 | 4 | 3 | 0 | 3 | 0 |
| 33 | 0 | 3 | 4 | 4 | 0 | 3 | 0 |
| 34 | 0 | 2 | 4 | 4 | 0 | 2 | 2 |
| 35 | 0 | 4 | 4 | 0 | 1 | — | — |
| 36 | 0 | 4 | 4 | 4 | 1 | — | — |
| 37 | 0 | 1 | 2 | 0 | 0 | 0 | 0 |
| 38 | 0 | 3 | 4 | 4 | 1 | — | — |
| 39 | 0 | 0 | 4 | 3 | — | 1 | 0 |
| 41 | 0 | 3 | 2 | 4 | 0 | — | — |
| 42 | 0 | 2 | 4 | 4 | 0 | — | — |
| 43 | 0 | 3 | 4 | 1 | 1 | — | — |
| 44 | 0 | 3 | 4 | 4 | 0 | — | — |
| 45 | 0 | 2 | 4 | 2 | 1 | — | — |

TABLE 6-continued

| COMPOUND NUMBER | PUCCINIA BECONDITA (WHEAT) | ERYSIPHE GRAMINIS (BARLEY) | PLASMOPARA VITICOLA (VINE) | PHYTOPHTHORA INFESTANS (TOMATO) | BOTRYTIS CINEREA (TOMATO) | CERCOSPORA ARACHIDICOLA (PEANUT) | VENTURIA INEQUALIS (APPLE) |
|---|---|---|---|---|---|---|---|
| 46 | — | 0 | 0 | 2 | 0 | 0 | 0 |
| 47 | — | 0 | 2 | 3 | 0 | 0 | 1 |
| 48 | — | 0 | 0 | 0 | 1 | 2 | 0 |
| 49 | — | 0 | 0 | 2 | 0 | 0 | 0 |
| 50 | 0 | 3 | 0 | 0 | 0 | — | — |
| 51 | 0 | 0 | 4 | 4 | 1 | — | — |
| 52 | 0 | 0 | 4 | 3 | 1 | — | — |
| 53 | — | 0 | 0 | 0 | 0 | 2 | 0 |
| 54 | — | 4 | 0 | 0 | 0 | 0 | 2 |
| 55 | — | 4 | 1 | 0 | 0 | 2 | 4 |
| 56 | 0 | 1 | 0 | 0 | — | 0 | 0 |
| 57 | 0 | 0 | 0 | 0 | 0 | 0 | 0 |
| 59 | — | — | — | — | — | — | — |
| 60 | 0 | 1 | — | 2 | 0 | 3 | 0 |
| 61 | 0 | 1 | — | 4 | 1 | 4 | 1 |
| 62 | 0 | 1 | — | 4 | 2 | 4 | 0 |
| 63 | 0 | 4 | — | 4 | 2 | 1 | 0 |
| 64 | 0 | 2 | — | 0 | 1 | 1 | 0 |
| 65 | 0 | 2 | — | 4 | 1 | 1 | 1 |
| 66 | 0 | 2 | — | 4 | 0 | 2 | 1 |
| 67 | 0 | 1 | 0 | 0 | 2 | 0 | 0 |
| 68 | 0 | — | 0 | 0 | 0 | 1 | 0 |
| 69 | 0 | 0 | — | 3 | 0 | 2 | 0 |
| 70 | 0 | 2 | 0 | 3 | 0 | 4 | — |
| 71 | 0 | 3 | — | 3 | 0 | 3 | 3 |
| 72 | 0 | 4 | 0 | 0 | 0 | 0 | 1 |
| 73 | 0 | 0 | 0 | 0 | 0 | 1 | 0 |
| 74 | 0 | 1 | 0 | 0 | 0 | 0 | 0 |
| 75 | 0 | 0 | 0 | 0 | 0 | 0 | 0 |
| 76 | 0 | 0 | 0 | 0 | 0 | 0 | 0 |
| 77 | 0 | 0 | 0 | 0 | 0 | 0 | 0 |
| 78 | 0 | 0 | 1 | 0 | 0 | 0 | 0 |
| 79 | 0 | 0 | 0 | 0 | 0 | 0 | 3 |
| 80 | 0 | 0 | 0 | 0 | 0 | 0 | 0 |
| 81 | 0 | 0 | 4 | 3 | 0 | 2 | 0 |
| 82 | 0 | 0 | 1 | 0 | 0 | 0 | 0 |
| 83 | 0 | 0 | 3 | 2 | 0 | 1 | 0 |
| 84 | 0 | 0 | 4 | 1 | 0 | 0 | 0 |
| 85 | 0 | 0 | 4 | 4 | 0 | 0 | 2 |
| 86 | 0 | 0 | 3 | 0 | 0 | 2 | 2 |
| 87 | — | — | — | — | — | — | — |
| 89 | 0 | 2 | 0 | 0 | 1 | 0 | 0 |
| 90 | 0 | 0 | 0 | 0 | 0 | 1 | 0 |
| 91 | 0 | 0 | 4 | 4 | 1 | 0 | 0 |
| 92 | 0 | 1 | 4 | 3 | 0 | 0 | 0 |
| 93 | 1 | 3 | 0 | 0 | 3 | 2 | 0 |
| 94 | — | — | — | — | — | — | — |
| 95 | 0 | 0 | 4 | 4 | 2 | 0 | — |
| 96 | 0 | 0 | 3 | 4 | 0 | 0 | 0 |
| 97 | 0 | 0 | 4 | 4 | 0 | 0 | 0 |
| 98 | 0 | 0 | 4 | 4 | 0 | 0 | 2 |
| 99 | 0 | 0 | 0 | 3 | 0 | 0 | 0 |
| 100 | 0 | 0 | 1 | 0 | 0 | 0 | 0 |
| 101 | 0 | 1 | 0 | 0 | 0 | 0 | 0 |
| 102 | 0 | 0 | 4 | 4 | 0 | 2 | 0 |
| 103 | 0 | 0 | 0 | 0 | 0 | 0 | 2 |
| 104 | — | — | — | — | — | — | — |
| 105 | 0 | 0 | 0 | 0 | 0 | 0 | 0 |
| 106 | 0 | 0 | 0 | 0 | 0 | 0 | 0 |
| 107 | 0 | 0 | 0 | 0 | 0 | 0 | 0 |
| 108 | 1 | 0 | 4 | 0 | 0 | 0 | 0 |
| 109 | 0 | 0 | 4 | 4 | 0 | 3 | 0 |
| 110 | 0 | 0 | 4 | 4 | 0 | 0 | 0 |
| 111 | 0 | 0 | 4 | 4 | 0 | 2 | 0 |
| 112 | 0 | 0 | 1 | 0 | 0 | 0 | 0 |
| 113 | 0 | 0 | 0 | 1 | 0 | 0 | 0 |
| 114 | 0 | 0 | 0 | 0 | — | 0 | 0 |
| 115 | 0 | 0 | 0 | 1 | 0 | 0 | 0 |
| 117 | 0 | 0 | 4 | 4 | 0 | 2 | 0 |
| 118 | 0 | 0 | 4 | 3 | 0 | 3 | — |
| 119 | 0 | 0 | 4 | 3 | 0 | 0 | 0 |
| 120 | 0 | 0 | 4 | 4 | 0 | 2 | 0 |
| 121 | 0 | 0 | 0 | 0 | 0 | 0 | 0 |
| 122 | 0 | 0 | 0 | 0 | 0 | 0 | 0 |
| 124 | 0 | 0 | 2 | 0 | 2 | 0 | 0 |
| 125 | 0 | 0 | 4 | 4 | 0 | 0 | 0 |
| 126 | 0 | 0 | 4 | 3 | 0 | 2 | 0 |
| 127 | 0 | 0 | 0 | 0 | 2 | 0 | 0 |
| 128 | 0 | 0 | 0 | 0 | 1 | 0 | 0 |

| COMPOUND NUMBER | PUCCINIA BECONDITA (WHEAT) | ERYSIPHE GRAMINIS (BARLEY) | PLASMOPARA VITICOLA (VINE) | PHYTOPHTHORA INFESTANS (TOMATO) | BOTRYTIS CINEREA (TOMATO) | CERCOSPORA ARACHIDICOLA (PEANUT) | VENTURIA INEQUALIS (APPLE) |
|---|---|---|---|---|---|---|---|

TABLE 6-continued

| COMPOUND NUMBER | PUCCINIA BECONDITA (WHEAT) | ERYSIPHE GRAMINIS (BARLEY) | PLASMOPARA VITICOLA (VINE) | PHYTOPHTHORA INFESTANS (TOMATO) | BOTRYTIS CINEREA (TOMATO) | CERCOSPORA ARACHIDICOLA (PEANUT) | VENTURIA INEQUALIS (APPLE) |
|---|---|---|---|---|---|---|---|
| 129 | 1 | 0 | 0 | 0 | 2 | 1 | 0 |
| 130 | 4 | 2 | 3 | 0 | 2 | 2 | 0 |
| 131 | 3 | 0 | 2 | 0 | 1 | 0 | 0 |
| 132 | — | — | — | — | — | — | — |
| 133 | 0 | 0 | 0 | 0 | 0 | 2 | 0 |
| 134 | 0 | 1 | 4 | 4 | 0 | 3 | 2 |
| 137 | 0 | 0 | 0 | — | 0* | 0 | 0 |
| 139 | 0 | 0 | 0 | — | 0* | 0 | 0 |
| 141 | 0 | 0 | 4 | — | 0* | — | 0 |
| 146 | 0 | 1 | 3 | 2 | 0* | 0 | 0 |
| 149 | 0 | 3 | 0 | 0 | 0* | 1 | 0 |
| 150 | 0 | 2 | 0 | 0 | 0* | 0 | 2 |
| 151 | 0 | 0 | 2 | 1 | 0* | 3 | 0 |
| 152 | 0 | 0 | 0 | 0 | 0* | 3 | 0 |
| 153 | 0 | 0 | 1 | 3 | 0* | 4 | 0 |
| 154 | 0 | 0 | 1 | 0 | 0* | 3 | 1 |
| 155 | 0 | 0 | 4 | 2 | 0* | 4 | 0 |
| 156 | 0 | 0 | 0 | 0 | 0* | 3 | 0 |
| 157 | 0 | 0 | 0 | 0 | 0* | 2 | 0 |
| 158 | 0 | 0 | 4 | 4 | 0* | 4 | 0 |
| 159 | 0 | 0 | 0 | 0 | 0* | 3 | 0 |
| 161 | 0 | 2 | 0 | 0 | 0 | 0 | 0 |
| 162 | 0 | 2 | 0 | 0 | 0 | 0 | 0 |
| 163 | 0 | 1 | 0 | 0 | 0 | 0 | 0 |
| 164 | 0 | 3 | 0 | 0 | 0 | 0 | 0 |
| 165 | 0 | 4 | 0 | 0 | 0 | 0 | 0 |
| 166 | 0 | 0 | 0 | | 0 | 0 | 0 |
| 167 | 0 | 3 | 3 | 3 | 0 | 2 | 0 |
| 169 | 0 | 0 | 1 | 0 | 0 | 0 | 0 |
| 171 | 0 | 2 | 0 | 0 | 0 | 0 | 0 |
| 172 | 0 | 0 | 2 | 0 | 0 | 0 | 0 |
| 173 | 0 | 0 | 0 | 0 | 0 | 0 | 0 |
| 174 | 0 | 0 | 4 | 3 | 0 | 0 | 2 |
| 175 | 0 | 0 | 4 | 4 | 0 | 0 | 0 |
| 176 | 0 | 0 | 1 | | 0 | 2 | 0 |
| 177 | 0 | 0 | 0 | | 0 | 0 | 0 |
| 178 | 0 | 1 | 0 | | 0 | 0 | 0 |
| 179 | 0 | 1 | 0 | | 0 | 0 | 0 |
| 180 | 0 | 3 | 0 | | 0 | 0 | 0 |
| 181 | 0 | 4 | 4 | | 0 | 0 | 0 |
| 182 | 0 | 0 | 0 | | 0 | 0 | 0 |
| 183 | 0 | 0 | 0 | | 0 | 0 | 0 |
| 184 | 0 | 0 | 0 | | 0 | 0 | 0 |
| 185 | 0 | 0 | 0 | | 0 | 0 | 0 |
| 186 | 0 | 1 | 4 | | 0 | 0 | 0 |
| 187 | 0 | 0 | 0 | | 0 | 0 | 0 |
| 188 | 0 | 0 | 0 | | 0 | 0 | 0 |
| 189 | 0 | 0 | 0 | | 0 | 0 | 0 |
| 190 | 0 | 0 | 4 | | 0 | 0 | 0 |
| 191 | 0 | 0 | 0 | | 0 | 0 | 0 |
| 192 | 0 | 2 | 3 | | 0 | 0 | 0 |
| 193 | 0 | 0 | 0 | | 0 | 0 | 0 |
| 194 | 0 | 1 | 0 | | 0 | 0 | 2 |
| 195 | 0 | 1 | 0 | | 0 | 0 | 3 |

We claim:
1. Amide derivative of the formula (I)

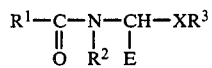

wherein $R^1$ is an optionally substituted alkyl, alkenyl, aryl, heterocyclyl, benzyl, or heterocyclylmethyl radical;
$R^2$ is hydrogen, or an optionally substituted alkyl, alkenyl, benzyl or heterocyclylmethyl radical;
X is oxygen, sulphur or an —NH— group;
$R^3$ is an optionally substituted alkyl or alkenyl radical when X is oxygen or sulphur, or is an optionally substituted alkanoyl radical when X is —NH—;
and E is a —CN, —CONH$_2$, —CSNH$_2$, or —CONR$^4$R$^5$ group wherein each $R^4$ and $R^5$ is an optionally substituted alkyl or alkenyl group provided that E is not —CN when $R^1$ is optionally substituted phenyl and X is oxygen or sulphur and provided further when $R^1$ is aryl, $R^2$ is hydrogen, $R^3$ is alkyl, X is sulphur and E is cyano or —CONH$_2$, the $R^1$ aryl is halo-phenyl.

2. Amide derivatives according to claim 1 wherein $R^1$ is an optionally substituted $C_{1-5}$ alkyl or $C_{3-5}$ alkenyl radical; a phenyl, naphthyl or benzyl radical each optionally substituted in the ring with fluorine, chlorine, bromine or iodine, $C_{1-4}$ alkyl, $C_{1-4}$ alkoxy, methylenedioxy, ethylenedioxy, $C_{1-4}$ alkylthio, nitro, cyano or $C_{1-4}$ haloalkyl; an optionally substituted furyl, thienyl, pyridyl, thiazolyl, or benzthiazolyl radical; or an optionally substituted heterocyclylmethyl radical wherein the heterocyclyl group is furyl, thienyl, pyridyl, thiazolyl or benzthiazolyl; $R^2$ is hydrogen, $C_{1-4}$ alkyl, allyl, phenyl, benzyl or a furylmethyl group; $R^3$ is $C_{1-4}$ alkyl, $C_{1-4}$ haloalkyl or $C_{3-4}$ alkenyl radical, or is a $C_{1-4}$ alkanoyl group when X is NH; and each $R^4$ and $R^5$ is methyl.

3. Amide derivatives according to claim 1 wherein $R^1$ is an optionally substituted aryl or heterocyclic group.

4. Amide derivatives according to claim 1 wherein $R^1$ is phenyl optionally substituted at any of the 3-, 4- or 5-position with an alkyl, alkoxy or methylenedioxy group or with halogen.

5. Amide derivatives according to claim 1 wherein $R^1$ is furyl, benzfuryl, thienyl, pyridyl, thiazolyl or benzthiazolyl.

6. Amide derivatives according to claim 1 wherein $R^2$ is hydrogen.

7. Amide derivatives according to claim 1 wherein $R^3$ is allyl or a $C_{1-4}$ alkyl group.

8. Amide derivatives according to claim 1 wherein X is oxygen or sulphur.

9. Amide derivatives according to claim 1 wherein X is oxygen.

10. Amide derivatives according to claim 1 wherein E is CN or $CSNH_2$.

11. A pesticidal composition, and especially fungicidal and herbicidal compositions, comprising as an active ingredient an amide derivative as defined in claim 1 together with a carrier or diluent.

12. A process of inhibiting the growth of unwanted plants, which comprises applying to the plants, or to the locus thereof, a phytotoxic amount of a compound as defined in claim 1.

13. A process for combating fungi which comprises applying to the fungi, or the locus thereof, a fungicidally effective amount of a compound as defined in claim 1.

14. A method of combating fungal disease in a plant which comprises applying to the plant, to the seed of the plant, or to the locus of the plant, or seed, a compound as defined in claim 1.

15. An amide derivative of the formula (I):

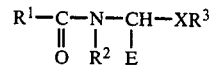

wherein $R^1$ is phenyl substituted with cyano;
$R^2$ is hydrogen, $C_1-C_4$ alkyl or $C_3-C_5$ alkenyl;
X is oxygen or sulphur;
$R^3$ is lower alkyl, lower haloalkyl or lower alkenyl; and
E is —CN.

* * * * *